US009266845B2

(12) United States Patent
Riggs-Sauthier et al.

(10) Patent No.: US 9,266,845 B2
(45) Date of Patent: Feb. 23, 2016

(54) OLIGOMER-CONTAINING SUBSTITUTED AROMATIC TRIAZINE COMPOUNDS

(71) Applicant: NEKTAR THERAPEUTICS, San Francisco, CA (US)

(72) Inventors: Jennifer Riggs-Sauthier, San Francisco, CA (US); Bo-Liang Deng, San Ramon, CA (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

(21) Appl. No.: 14/528,444

(22) Filed: Oct. 30, 2014

(65) Prior Publication Data

US 2015/0065706 A1    Mar. 5, 2015

Related U.S. Application Data

(63) Continuation of application No. 14/282,732, filed on May 20, 2014, now Pat. No. 8,895,553, which is a continuation of application No. 13/319,824, filed as application No. PCT/US2010/034770 on May 13, 2010, now Pat. No. 8,772,479.

(60) Provisional application No. 61/177,931, filed on May 13, 2009.

(51) Int. Cl.
| | |
|---|---|
| *C07D 253/075* | (2006.01) |
| *A61K 31/53* | (2006.01) |
| *A61P 35/00* | (2006.01) |
| *A61K 47/48* | (2006.01) |

(52) U.S. Cl.
CPC ...... *C07D 253/075* (2013.01); *A61K 47/48215* (2013.01); *A61K 31/53* (2013.01)

(58) Field of Classification Search
CPC .............................. C07D 253/075; A61K 31/53
USPC ........................................ 544/182; 514/242
See application file for complete search history.

(56) References Cited

U.S. PATENT DOCUMENTS

| | | | |
|---|---|---|---|
| 4,602,017 A | 7/1986 | Sawyer et al. | |
| 4,810,646 A | 3/1989 | Jamas et al. | |
| 4,992,540 A | 2/1991 | Jamas et al. | |
| 5,028,703 A | 7/1991 | Jamas et al. | |
| 5,607,677 A | 3/1997 | Jamas et al. | |
| 5,672,662 A | 9/1997 | Harris et al. | |
| 5,741,495 A | 4/1998 | Jamas et al. | |
| 6,395,266 B1 | 5/2002 | Martinez et al. | |
| 7,678,551 B2 | 3/2010 | Ouyang et al. | |
| 7,816,520 B2 | 10/2010 | Picoul et al. | |
| 8,772,479 B2 * | 7/2014 | Riggs-Sauthier et al. | .... 544/182 |
| 8,895,553 B2 * | 11/2014 | Riggs-Sauthier et al. | .... 514/242 |
| 2002/0182172 A1 | 12/2002 | Bentley et al. | |
| 2005/0136031 A1 | 6/2005 | Bentley et al. | |
| 2005/0281781 A1 | 12/2005 | Ostroff | |
| 2006/0115865 A1 | 6/2006 | Ouyang et al. | |
| 2008/0044438 A1 | 2/2008 | Ostroff et al. | |
| 2012/0122871 A1 | 5/2012 | Riggs-Sauthier et al. | |
| 2014/0256732 A1 | 9/2014 | Riggs-Sauthier et al. | |

FOREIGN PATENT DOCUMENTS

| | | |
|---|---|---|
| WO | WO 02/43772 | 6/2002 |
| WO | WO 02/098949 | 12/2002 |
| WO | WO 2006/027711 | 3/2006 |
| WO | WO 2006/047372 | 5/2006 |

OTHER PUBLICATIONS

Chen, et al., "Synthesis and Properties of ABA Amphiphiles," J. Org. Chem., vol. 64, pp. 6870-6873, (1999).
Doig, et al., "Use of thermospray liquid chromatography-mass spectrometry to aid in the identification . . . ," J. of Chromatography, vol. 554, pp. 181-189, (1991).
Ertl, et al., "Fast Calculation of Molecular Polar Surface Area as a Sum of Fragment-Based Contributions . . . ," J. Med. Chem., vol. 43, pp. 3714-3717, (2000).
Juergens, "Alkylamine/Phosphoric Acid as a Universal Buffer System for Basic and Acidic . . . ," J. of Liquid Chromatography, vol. 11, No. 9 & 10, pp. 1925-1940, (1988).
Kelder, et al., "Polar Molecular Surface as a Dominating Determinant for Oral Absorption and Brain . . . ," Pharmaceu. Res., vol. 16, No. 10, pp. 1514-1519, (1999).
Nyffenegger, et al., "Synthesis of 3-amino-5H-pyrrolo[2,3-e]-1,2,4-triazines by Sonogashira/copper(I)-catalyzed . . . ," Tetrahedron Lett., vol. 48, pp. 5069-5072, (2007).
Woodbury, et al., "Design and Use of a New Electroshock Seizure Apparatus, and Analysis of Factors . . . ," Arch. Int. Pharmacodyn., vol. 92, No. 1, pp. 97-104, (1952).
XP002597917, "Alkylamine/phosphoric acid as a universal buffer system for basic . . . ," Database HCAPLUS [Online], Database accession No. 110:101940(DN), 1 page, (1989).
PCT International Search Report corresponding to PCT Application No. PCT/US2010/034770 date of mailing Sep. 15, 2010.
PCT International Preliminary Report on Patentability corresponding to PCT Application No. PCT/US2010/034770 date of mailing Nov. 24, 2011.
Notification of the First Office Action corresponding to Chinese Patent Application No. 201080020581.5 dated Oct. 12, 2013.
Enzon Pharmaceuticals, Macromolecular Engineering Technologies, 16 pages, (2004).
Nektar™—Transforming Therapeutics, Nektar Molecule Engineering: Polyethylene Glycol and Derivatives for Advanced PEGylation, 24 pages, Catalog—2003, (Jul. 2003).

(Continued)

*Primary Examiner* — Venkataraman Balasubramanian
(74) *Attorney, Agent, or Firm* — Mark A. Wilson

(57) ABSTRACT

The invention relates to (among other things) methods for treatment comprising administering oligomer-containing substituted aromatic triazine compounds. A compound of the invention, when administered by any of a number of administration routes, exhibits one or more advantages over corresponding compounds lacking the oligomer.

14 Claims, No Drawings

(56) References Cited

OTHER PUBLICATIONS

Nektar™—Transforming Therapeutics, Nektar Advanced PEGylation: Polyethylene Glycol and Derivatives for Advanced PEGylation, 27 pages, Catalog—2004, (Jul. 2004).
Nektar™—Transforming Therapeutics, Nektar Advanced PEGylation: Polyethylene Glycol and Derivatives for Advanced PEGylation, 33 pages, (Catalog 2005-2006).
NOF Corporation, PEG Derivatives, Phospholipid and Drug Delivery Materials for Pharmaceuticals, pp. 1-46, Catalogue 2003—1st, (Jan. 2003).
NOF Corporation, PEG Derivatives, Phospholipid and Drug Delivery Materials for Pharmaceuticals, pp. 1-50, Catalogue 2003—2nd, (Mar. 2004).
NOF Corporation, PEG Derivatives, Phospholipids and Drug Delivery Materials for Pharmaceutical Products and Formulations, 60 pages, Catalogue Ver. 8, (Apr. 2006).
Polypure Products, PEG amines; PEG acids and amino acids; PEG thiols and disulfides; Biotins, 5 pages, (Apr. 2004).
Polypure Products, PEG amines; PEG acids and amino acids; PEG thiols and disulfides; Biotins, 5 pages, (Apr. 2005).
Quanta Biodesign, Labeling, Derivatization and Crosslinking Reagents for Biological and Related Materials with dPEG™, pp. 1-38, (Mar. 12, 2004).
Quanta Biodesign, Labeling, Modification and Crosslinking Reagents incorporating our unique monodispersed dPEG™ Technology, pp. 1-31, (Nov. 5, 2004).
Quanta Biodesign, Ltd., Leading innovator, producer and provider of monodisperse discrete PEG™ (dPEG™) derivatives, (Product Catalog), pp. 1-51, (Updated: Jul. 18, 2005).
Quanta Biodesign, Ltd., Leading innovator, producer and provider of monodisperse discrete PEG™ (dPEG™) derivatives, (Product Catalog), pp. 1-51, (Updated: Nov. 17, 2005).
Shearwater Polymers, Inc., Polyethylene Glycol and Derivatives, 50 pages, (Catalog—Mar. 1995).
Shearwater Polymers, Inc., Polyethylene Glycol and Derivatives, 55 pages, (Catalog—Jul. 1997).
Shearwater Polymers, Inc., Polyethylene Glycol and Derivatives: Functionalized Biocompatible Polymers for Research and Pharmaceuticals, pp. 1-50, (Catalog—Jan. 2000).
Shearwater Corporation, Polyethylene Glycol and Derivatives for Biomedical Applications, pp. 1-17, (Catalog—Jul. 2001).
Lawecka, et al., "Sequential homo-coupling Diels-Alder/*retro* Diels-Alder reaction of 5,5'-bi-1,2,4-triazine-containing thiamacrocylces as a new route to thiacrown ethers incorporating a 2,2'-bipyridine subunit", Tetrahedron Letters, vol. 49, pp. 723-726, (2008).
Chinese Notification of the Second Office Action corresponding to Chinese Patent Application No. 201080020581.5 date of notification Aug. 13, 2014.
Japanese Notice of Reasons for Rejection corresponding to Japanese Patent Application No. 2012-511017 mailing date Jun. 16, 2014.
Australian Patent Examination Report No. 1 corresponding to Australian Patent Application No. 2010248943 date of issue Sep. 24, 2014.
Israel First Substantive Examination Report corresponding to Israel Patent Application No. 216314 dated Dec. 17, 2014.
Mexico $1^{st}$ Substantive Examination Report corresponding to Mexico Patent Application No. MX/a/2011/012044 dated Mar. 13, 2015.
Mexico $2^{nd}$ Substantive Examination Report corresponding to Mexico Patent Application No. MX/a/2011/012044 dated Jun. 15, 2015.

\* cited by examiner

OLIGOMER-CONTAINING SUBSTITUTED AROMATIC TRIAZINE COMPOUNDS

CROSS REFERENCE TO RELATED APPLICATIONS

This application is a continuation of U.S. patent application Ser. No. 14/282,732, filed May 20, 2014, which is a continuation of U.S. patent application Ser. No. 13/319,824, filed Jan. 9, 2012, now U.S. Pat. No. 8,772,479, which is a 35 U.S.C. §371 application of International Application No. PCT/US2010/034770, filed 13 May 2010, designating the United States, which claims the benefit of priority under 35 U.S.C. §119(e) to U.S. Provisional Patent Application No. 61/177,931, filed May 13, 2009, the disclosures of which are incorporated herein by reference in their entireties.

FIELD OF THE INVENTION

This invention comprises (among other things) chemically modified substituted aromatic triazines that possess certain advantages over substituted aromatic triazines lacking the chemical modification. The chemically modified substituted aromatic triazines described herein relate to and/or have application(s) in (among others) the fields of drug discovery, pharmacotherapy, physiology, organic chemistry and polymer chemistry.

BACKGROUND OF THE INVENTION

Epilepsy is a common chronic neurological disorder characterized by recurrent unprovoked seizures. These seizures are transient signs and/or symptoms of abnormal, excessive or synchronous neuronal activity in the brain. About 50 million people worldwide have epilepsy, with almost 90% of these people being in developing countries. Epilepsy is more likely to occur in young children or people over the age of 65 years; however it can occur at any age. Epilepsy is usually controlled, but not cured, with pharmacotherapy, although surgery may be indicated in exceptional cases. Despite the reliance on pharmacotherapy as the primary approach in controlling the disease, over 30% of people with epilepsy do not have seizure control even with the best available medications. Not all epilepsy syndromes are life-long; some forms are confined to particular stages of childhood. Epilepsy should not be understood as a single disorder, but rather as a group of syndromes with vastly divergent symptoms, but all involving episodic abnormal electrical activity in the brain.

Seizure types are organized firstly according to whether the source of the seizure within the brain is localized (partial or focal onset seizures) or distributed (generalized seizures). Partial seizures are further divided on the extent to which consciousness is affected. If it is unaffected, then it is a simple partial seizure; otherwise it is a complex partial (psychomotor) seizure. A partial seizure may spread within the brain—a process known as secondary generalization. Generalized seizures are divided according to the effect on the body but all involve loss of consciousness. These include absence (petit mal), myoclonic, clonic, tonic, tonic-clonic (grand mal) and atonic seizures.

There are over 40 different types of epileptic conditions, including: absence seizures, atonic seizures, benign Rolandic epilepsy, childhood absence, clonic seizures, complex partial seizures, frontal lobe epilepsy, febrile seizures, infantile spasms, juvenile myoclonic epilepsy, juvenile absence epilepsy, Lennox-Gastaut syndrome, Landau-Kleffner syndrome, myoclonic seizures, mitochondrial disorders, progressive myoclonic epilepsies, psychogenic seizures, reflex epilepsy, Rasmussen's syndrome, simple partial seizures, secondarily generalized seizures, temporal lobe epilepsy, toni-clonic seizures, tonic seizures, psychomotor seizures, limbic epilepsy, partial-onset seizures, generalized-onset seizures, status epilepticus, abdominal epilepsy, akinetic seizures, auto-nomic seizures, massive bilateral myoclonus, catamenial epilepsy, drop seizures, emotional seizures, focal seizures, gelastic seizures, Jacksonian march, Lafora disease, motor seizures, multifocal seizures, neonatal seizures, nocturnal seizures, photosensitive seizure, pseudo seizures, sensory seizures, subtle seizures, Sylvan seizures, withdrawal seizures, and visual reflex seizures, among others.

Anticonvulsants are generally prescribed for the treatment of individuals suffering from or prone to epilepsy. Triazine compounds comprising substituted aromatic groups represent one such class of compounds. Triazine compounds are also used in the treatment of individuals suffering from bipolar I disorder, peripheral neuropathy, trigeminal neuralgia, cluster headaches, migraines, and neuropathic pain, depersonalization disorder, bipolar II disorders, schizoaffective disorder, borderline personality disorder, post traumatic stress disorder, and refractory unipolar depression. Treatment with this class of compounds, however, suffer from many side effects, including life threatening skin reactions, including Stevens-Johnson syndrome, toxic epidermal necrolysis, headaches, dizziness and insomnia. Other side effects may include acne and skin irritation, vivid dreams or nightmares, night sweats, body aches and cramps, muscle aches, dry mouth, fatigue, memory problems, cognitive problems, irritability, weight changes, hair loss, changes in libido, frequent urination, and nausea.

Therefore, pharmacotherapy with such therapeutic substituted aromatic triazines would be improved if these and/or other adverse or side effects associated with their use could be decreased or if their pharmacology may be improved. Thus, there is a large unmet need for developing novel substituted aromatic triazine compounds.

The present invention seeks to address these and other needs in the art.

SUMMARY OF THE INVENTION

In one or more embodiments of the invention, a compound is provided, the compound comprising a substituted aromatic triazine residue covalently attached via a stable or degradable linkage to a water-soluble, non-peptidic oligomer.

The "substituted aromatic triazine residue" is a compound having a structure of a therapeutically active substituted aromatic triazine moiety that is altered by the presence of one or more bonds, which bonds serve to attach (either directly or indirectly) one or more water-soluble, non-peptidic oligomers.

Exemplary compounds of the invention include those having the following structure:

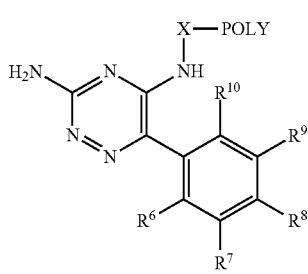

(Formula Ia-C)

wherein:

with respect to $R^6$ and $R^7$, either (i) $R^6$ is selected from the group consisting of halo, $C_{1-4}$ alkyl and trifluoromethyl and $R^7$ is selected from the group consisting of hydrogen, halo, $C_{1-4}$ alkyl and trifluoromethyl, or (ii) $R^6$ and $R^7$ combine to form —CH=CH—CH=CH— optionally substituted by halo, $C_{1-4}$ alkyl or trifluoromethyl;

$R^8$ is selected from the group consisting of hydrogen, halo, $C_{1-4}$ alkyl and trifluoromethyl;

$R^9$ is selected from the group consisting of hydrogen, halo, $C_{1-4}$ alkyl and trifluoromethyl;

$R^{10}$ is selected from the group consisting of hydrogen, halo, $C_{1-4}$ alkyl and trifluoromethyl;

X is a spacer moiety; and

POLY is a water-soluble, non-peptidic oligomer.

Further exemplary compounds of the invention include those having the following structure:

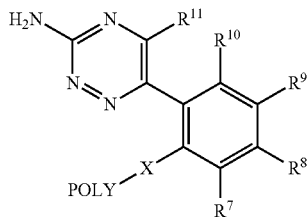

(Formula Ib¹-C)

wherein:

$R^7$ is selected from the group consisting of hydrogen, halo, $C_{1-4}$ alkyl and trifluoromethyl;

$R^8$ is selected from the group consisting of hydrogen, halo, $C_{1-4}$ alkyl and trifluoromethyl;

$R^9$ is selected from the group consisting of hydrogen, halo, $C_{1-4}$ alkyl and trifluoromethyl;

$R^{10}$ is selected from the group consisting of hydrogen, halo, $C_{1-4}$ alkyl and trifluoromethyl;

$R^{11}$ is selected from the group consisting of amino, $C_{1-10}$ acylamino and di-substituted aminomethyleneamino;

X is a spacer moiety; and

POLY is a water-soluble, non-peptidic oligomer.

Still further exemplary compounds of the invention include those having the following structure:

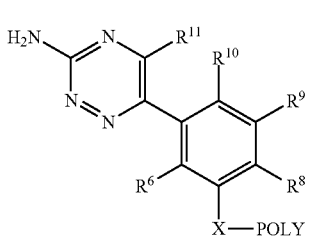

(Formula Ib²-C)

wherein:

$R^6$ is selected from the group consisting of halo, $C_{1-4}$ alkyl and trifluoromethyl;

$R^8$ is selected from the group consisting of hydrogen, halo, $C_{1-4}$ alkyl and trifluoromethyl;

$R^9$ is selected from the group consisting of hydrogen, halo, $C_{1-4}$ alkyl and trifluoromethyl;

$R^{10}$ is selected from the group consisting of hydrogen, halo, $C_{1-4}$ alkyl and trifluoromethyl;

$R^{11}$ is selected from the group consisting of amino, $C_{1-10}$ acylamino and di-substituted aminomethyleneamino;

X is a spacer moiety; and

POLY is a water-soluble, non-peptidic oligomer.

Still further exemplary compounds of the invention include those having the following structure:

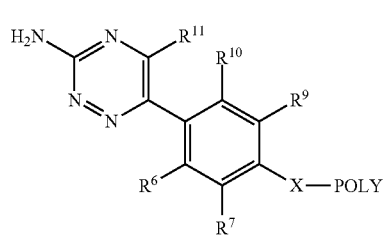

(Formula Ib³-C)

wherein:

with respect to $R^6$ and $R^7$, either (i) $R^6$ is selected from the group consisting of halo, $C_{1-4}$ alkyl and trifluoromethyl and $R^7$ is selected from the group consisting of hydrogen, halo, $C_{1-4}$ alkyl and trifluoromethyl, or (ii) $R^6$ and $R^7$ combine to form —CH=CH—CH=CH— optionally substituted by halo, $C_{1-4}$ alkyl or trifluoromethyl;

$R^9$ is selected from the group consisting of hydrogen, halo, $C_{1-4}$ alkyl and trifluoromethyl;

$R^{10}$ is selected from the group consisting of hydrogen, halo, $C_{1-4}$ alkyl and trifluoromethyl;

$R^{11}$ is selected from the group consisting of amino, $C_{1-10}$ acylamino and di-substituted aminomethyleneamino;

X is a spacer moiety; and

POLY is a water-soluble, non-peptidic oligomer.

In this regard, any substituted aromatic triazine compound having analgesic activity can be used as a substituted aromatic triazine moiety. Exemplary substituted aromatic triazine moieties have a structure encompassed by Formula I:

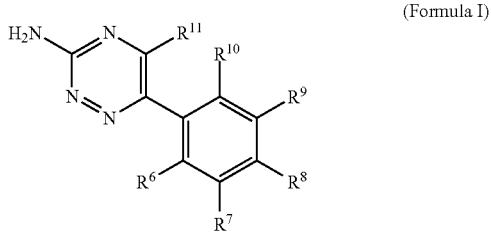

(Formula I)

wherein:

with respect to $R^6$ and $R^7$, either (i) $R^6$ is selected from the group consisting of halo, $C_{1-4}$ alkyl and trifluoromethyl and $R^7$ is selected from the group consisting of hydrogen, halo, $C_{1-4}$ alkyl and trifluoromethyl, or (ii) $R^6$ and $R^7$ combine to form —CH=CH—CH=CH— optionally substituted by halo, $C_{1-4}$ alkyl or trifluoromethyl;

$R^8$ is selected from the group consisting of hydrogen, halo, $C_{1-4}$ alkyl and trifluoromethyl;

$R^9$ is selected from the group consisting of hydrogen, halo, $C_{1-4}$ alkyl and trifluoromethyl;

$R^{10}$ is selected from the group consisting of hydrogen, halo, $C_{1-4}$ alkyl and trifluoromethyl; and $R^{11}$ is selected from the group consisting of amino, $C_{1-10}$ acylamino and di-substituted aminomethyleneamino.

An exemplary substituted aromatic triazine moiety is 6-(2,3-dichlorophenyl)-1,2,4-triazine-3,5-diamine, also conventionally named as 3,5-diamino-6-(2,3-dichlorophenyl)-1,2,4-triazine, which corresponds to the generic name lamotrigine (which is available from GlaxoSmithKline, London, United Kingdom).

In one or more embodiments of the invention, a composition is provided, the composition comprising a compound comprising a substituted aromatic triazine residue covalently attached via a stable or degradable linkage to a water-soluble, non-peptidic oligomer, and optionally, a pharmaceutically acceptable excipient.

In one or more embodiments of the invention, a dosage form is provided, the dosage form comprising a compound comprising a substituted aromatic triazine residue covalently attached via a stable or degradable linkage to a water-soluble, non-peptidic oligomer, wherein the compound is present in a dosage form.

In one or more embodiments of the invention, a method is provided, the method comprising covalently attaching a water-soluble, non-peptidic oligomer to a substituted aromatic triazine moiety.

In one or more embodiments of the invention, a method is provided, the method comprising administering a compound to a mammal in need thereof, the compound comprising a substituted aromatic triazine residue covalently attached via a stable or degradable linkage to a water-soluble, non-peptidic oligomer.

Additional embodiments of the present conjugates, compositions, methods, and the like will be apparent from the following description, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims.

DETAILED DESCRIPTION OF THE INVENTION

As used in this specification, the singular forms "a," "an," and "the" include plural referents unless the context clearly dictates otherwise.

In describing and claiming the present invention, the following terminology will be used in accordance with the definitions described below.

"Water soluble, non-peptidic oligomer" indicates an oligomer that is at least 35% (by weight) soluble, preferably greater than 70% (by weight), and more preferably greater than 95% (by weight) soluble, in water at room temperature. Typically, an unfiltered aqueous preparation of a "water-soluble" oligomer transmits at least 75%, more preferably at least 95%, of the amount of light transmitted by the same solution after filtering. It is most preferred, however, that the water-soluble oligomer is at least 95% (by weight) soluble in water or completely soluble in water. With respect to being "non-peptidic," an oligomer is non-peptidic when it has less than 35% (by weight) of amino acid residues.

The terms "monomer," "monomeric subunit" and "monomeric unit" are used interchangeably herein and refer to one of the basic structural units of a polymer or oligomer. In the case of a homo-oligomer, a single repeating structural unit forms the oligomer. In the case of a co-oligomer, two or more structural units are repeated—either in a pattern or randomly—to form the oligomer. Preferred oligomers used in connection with present the invention are homo-oligomers. The water-soluble, non-peptidic oligomer comprises one or more monomers serially attached to form a chain of monomers. The oligomer can be formed from a single monomer type (i.e., is homo-oligomeric) or two or three monomer types (i.e., is co-oligomeric).

An "oligomer" is a molecule possessing from about 1 to about 30 monomers. Specific oligomers for use in the invention include those having a variety of geometries such as linear, branched, or forked, to be described in greater detail below.

"PEG" or "polyethylene glycol," as used herein, is meant to encompass any water-soluble poly(ethylene oxide). Unless otherwise indicated, a "PEG oligomer" or an oligoethylene glycol is one in which substantially all (preferably all) monomeric subunits are ethylene oxide subunits, though, the oligomer may contain distinct end capping moieties or functional groups, e.g., for conjugation. PEG oligomers for use in the present invention will comprise one of the two following structures: "—$(CH_2CH_2O)_n$—" or "—$(CH_2CH_2O)_{n-1}CH_2CH_2$—," depending upon whether or not the terminal oxygen(s) has been displaced, e.g., during a synthetic transformation. As stated above, for the PEG oligomers, the variable (n) ranges from about 1 to 30, and the terminal groups and architecture of the overall PEG can vary. When PEG further comprises a functional group, A, for linking to, e.g., a small molecule drug, the functional group when covalently attached to a PEG oligomer does not result in formation of (i) an oxygen-oxygen bond (—O—O—, a peroxide linkage), or (ii) a nitrogen-oxygen bond (N—O, O—N).

The terms "end-capped" or "terminally capped" are interchangeably used herein to refer to a terminal or endpoint of a polymer having an end-capping moiety. Typically, although not necessarily, the end-capping moiety comprises a hydroxy or $C_{1-20}$ alkoxy group. Thus, examples of end-capping moieties include alkoxy (e.g., methoxy, ethoxy and benzyloxy), as well as aryl, heteroaryl, cyclo, heterocyclo, and the like. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) of interest to which the polymer is coupled, can be determined by using a suitable detector. Such labels include, without limitation, fluorescers, chemiluminescers, moieties used in enzyme labeling, colorimetric moieties (e.g., dyes), metal ions, radioactive moieties, and the like. Suitable detectors include photometers, films, spectrometers, and the like. In addition, the end-capping group may contain a targeting moiety.

The term "targeting moiety" is used herein to refer to a molecular structure that helps the conjugates of the invention to localize to a targeting area, e.g., help enter a cell, or bind a receptor. Preferably, the targeting moiety comprises of vitamin, antibody, antigen, receptor, DNA, RNA, sialyl Lewis X antigen, hyaluronic acid, sugars, cell specific lectins, steroid or steroid derivative, RGD peptide, ligand for a cell surface receptor, serum component, or combinatorial molecule directed against various intra- or extracellular receptors. The targeting moiety may also comprise a lipid or a phospholipid. Exemplary phospholipids include, without limitation, phosphatidylcholines, phosphatidylserine, phosphatidylinositol, phosphatidylglycerol, and phosphatidylethanolamine. These lipids may be in the form of micelles or liposomes and the like. The targeting moiety may further comprise a detectable label or alternately a detectable label may serve as a targeting moiety.

"Branched," in reference to the geometry or overall structure of an oligomer, refers to an oligomer having two or more polymer "arms" extending from a branch point.

"Forked," in reference to the geometry or overall structure of an oligomer, refers to an oligomer having two or more functional groups (typically through one or more atoms) extending from a branch point.

A "branch point" refers to a bifurcation point comprising one or more atoms at which an oligomer branches or forks from a linear structure into one or more additional arms.

The term "reactive" or "activated" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive," with reference to a functional group present on a molecule in a reaction mixture, indicates that the group remains largely intact under conditions that are effective to produce a desired reaction in the reaction mixture.

A "protecting group" is a moiety that prevents or blocks reaction of a particular chemically reactive functional group in a molecule under certain reaction conditions. The protecting group may vary depending upon the type of chemically reactive group being protected as well as the reaction conditions to be employed and the presence of additional reactive or protecting groups in the molecule. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

A functional group in "protected form" refers to a functional group bearing a protecting group. As used herein, the term "functional group" or any synonym thereof encompasses protected forms thereof.

A "physiologically cleavable" or "hydrolyzable" or "degradable" bond is a relatively labile bond that reacts with water (i.e., is hydrolyzed) under physiological conditions. The tendency of a bond to hydrolyze in water may depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides, oligonucleotides, thioesters, and carbonates.

An "enzymatically degradable linkage" means a linkage that is subject to degradation by one or more enzymes.

A "stable" linkage or bond refers to a chemical bond that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, amines, and the like. Generally, a stable linkage is one that exhibits a rate of hydrolysis of less than about 1-2% per day under physiological conditions. Hydrolysis rates of representative chemical bonds can be found in most standard chemistry textbooks.

"Substantially" or "essentially" means nearly totally or completely, for instance, 95% or greater, more preferably 97% or greater, still more preferably 98% or greater, even more preferably 99% or greater, yet still more preferably 99.9% or greater, with 99.99% or greater being most preferred of some given quantity.

"Monodisperse" refers to an oligomer composition wherein substantially all of the oligomers in the composition have a well-defined, single molecular weight and defined number of monomers, as determined by chromatography or mass spectrometry. Monodisperse oligomer compositions are in one sense pure, that is, substantially having a single and definable number (as a whole number) of monomers rather than a large distribution. A monodisperse oligomer composition possesses a MW/Mn value of 1.0005 or less, and more preferably, a MW/Mn value of 1.0000. By extension, a composition comprised of monodisperse conjugates means that substantially all oligomers of all conjugates in the composition have a single and definable number (as a whole number) of monomers rather than a large distribution and would possess a MW/Mn value of 1.0005, and more preferably, a MW/Mn value of 1.0000 if the oligomer were not attached to the therapeutic moiety. A composition comprised of monodisperse conjugates may, however, include one or more non-conjugate substances such as solvents, reagents, excipients, and so forth.

"Bimodal," in reference to an oligomer composition, refers to an oligomer composition wherein substantially all oligomers in the composition have one of two definable and different numbers (as whole numbers) of monomers rather than a large distribution, and whose distribution of molecular weights, when plotted as a number fraction versus molecular weight, appears as two separate identifiable peaks. Preferably, for a bimodal oligomer composition as described herein, each peak is generally symmetric about its mean, although the size of the two peaks may differ. Ideally, the polydispersity index of each peak in the bimodal distribution, Mw/Mn, is 1.01 or less, more preferably 1.001 or less, and even more preferably 1.0005 or less, and most preferably a MW/Mn value of 1.0000. By extension, a composition comprised of bimodal conjugates means that substantially all oligomers of all conjugates in the composition have one of two definable and different numbers (as whole numbers) of monomers rather than a large distribution and would possess a MW/Mn value of 1.01 or less, more preferably 1.001 or less and even more preferably 1.0005 or less, and most preferably a MW/Mn value of 1.0000 if the oligomer were not attached to the therapeutic moiety. A composition comprised of bimodal conjugates may, however, include one or more nonconjugate substances such as solvents, reagents, excipients, and so forth.

A "substituted aromatic triazine moiety" is broadly used herein to refer to an organic, inorganic, or organometallic compound having a molecular weight of less than about 1000 Daltons and having some degree of activity as an anticonvulsant and/or analgesic. Assays known to those of ordinary skill in the art can be used to determine whether a given substituted aromatic triazine moiety (as well as a compound as provided herein) has activity as an anticonvulsant and/or analgesic.

A "biological membrane" is any membrane made of cells or tissues that serves as a barrier to at least some foreign entities or otherwise undesirable materials. As used herein a "biological membrane" includes those membranes that are associated with physiological protective barriers including, for example: the blood-brain barrier (BBB); the blood-cerebrospinal fluid barrier; the blood-placental barrier; the blood-milk barrier; the blood-testes barrier; and mucosal barriers including the vaginal mucosa, urethral mucosa, anal mucosa, buccal mucosa, sublingual mucosa, and rectal mucosa. Unless the context clearly dictates otherwise, the term "biological membrane" does not include those membranes associated with the middle gastro-intestinal tract (e.g., stomach and small intestines).

A "biological membrane crossing rate," provides a measure of a compound's ability to cross a biological membrane, such as the blood-brain barrier ("BBB"). A variety of methods may be used to assess transport of a molecule across any given biological membrane. Methods to assess the biological membrane crossing rate associated with any given biological barrier (e.g., the blood-cerebrospinal fluid barrier, the blood-placental barrier, the blood-milk barrier, the intestinal barrier, and so forth), are known, described herein and/or in the relevant literature, and/or may be determined by one of ordinary skill in the art.

A "reduced rate of metabolism" refers to a measurable reduction in the rate of metabolism of a water-soluble oligomer-small molecule drug conjugate as compared to the rate of metabolism of the small molecule drug not attached to the water-soluble oligomer (i.e., the small molecule drug itself) or a reference standard material. In the special case of "reduced first pass rate of metabolism," the same "reduced rate of metabolism" is required except that the small molecule drug (or reference standard material) and the corresponding conjugate are administered orally. Orally administered drugs are absorbed from the gastro-intestinal tract into the portal circulation and may pass through the liver prior to reaching the systemic circulation. Because the liver is the primary site of drug metabolism or biotransformation, a substantial amount of drug may be metabolized before it ever reaches the systemic circulation. The degree of first pass metabolism, and thus, any reduction thereof, may be measured by a number of different approaches. For instance, animal blood samples may be collected at timed intervals and the plasma or serum analyzed by liquid chromatography/mass spectrometry for metabolite levels. Other techniques for measuring a "reduced rate of metabolism" associated with the first pass metabolism and other metabolic processes are known, described herein and/or in the relevant literature, and/or may be determined by one of ordinary skill in the art. Preferably, a compound of the invention may provide a reduced rate of metabolism [relative to a compound lacking any water-soluble, non-peptidic oligomer(s)] satisfying at least one of the following values: at least about 30%; at least about 40%; at least about 50%; at least about 60%; at least about 70%; at least about 80%; and at least about 90%. A compound (such as a small molecule drug or conjugate thereof) that is "orally bioavailable" is one that preferably possesses a bioavailability when administered orally of greater than 25%, and preferably greater than 70%, where a compound's bioavailability is the fraction of administered drug that reaches the systemic circulation in unmetabolized form.

"Alkyl" refers to a hydrocarbon chain, ranging from about 1 to 20 atoms in length. Such hydrocarbon chains are preferably but not necessarily saturated and may be branched or straight chain. Exemplary alkyl groups include methyl, ethyl, propyl, butyl, pentyl, 2-methylbutyl, 2-ethylpropyl, 3-methylpentyl, and the like. As used herein, "alkyl" includes cycloalkyl when three or more carbon atoms are referenced. An "alkenyl" group is an alkyl of 2 to 20 carbon atoms with at least one carbon-carbon double bond.

The terms "substituted alkyl" or "substituted $C_{q-r}$ alkyl" where q and r are integers identifying the range of carbon atoms contained in the alkyl group, denotes the above alkyl groups that are substituted by one, two or three halo (e.g., F, Cl, Br, I), trifluoromethyl, hydroxy, $C_{1-7}$ alkyl (e.g., methyl, ethyl, n-propyl, isopropyl, butyl, t-butyl, and so forth), $C_{1-7}$ alkoxy, $C_{1-7}$ acyloxy, $C_{3-7}$ heterocyclic, amino, phenoxy, nitro, carboxy, acyl, cyano. The substituted alkyl groups may be substituted once, twice or three times with the same or with different substituents.

"Lower alkyl" refers to an alkyl group containing from 1 to 6 carbon atoms, and may be straight chain or branched, as exemplified by methyl, ethyl, n-butyl, i-butyl, t-butyl. "Lower alkenyl" refers to a lower alkyl group of 2 to 6 carbon atoms having at least one carbon-carbon double bond.

"Non-interfering substituents" are those groups that, when present in a molecule, are typically non-reactive with other functional groups contained within the molecule.

"Alkoxy" refers to an —O—R group, wherein R is alkyl or substituted alkyl, preferably $C_1$-$C_{20}$ alkyl (e.g., methoxy, ethoxy, propyloxy, etc.), preferably $C_1$-$C_7$.

"Pharmaceutically acceptable excipient" or "pharmaceutically acceptable carrier" refers to component that may be included in the compositions of the invention causes no significant adverse toxicological effects to a patient.

The term "aryl" means an aromatic group having up to 14 carbon atoms. Aryl groups include phenyl, naphthyl, biphenyl, phenanthrenyl, naphthalenyl, and the like. "Substituted phenyl" and "substituted aryl" denote a phenyl group and aryl group, respectively, substituted with one, two, three, four or five (e.g., 1-2, 1-3 or 1-4 substituents) chosen from halo (e.g., F, Cl, Br, I), hydroxy, cyano, nitro, alkyl (e.g., $C_{1-6}$ alkyl), alkoxy (e.g., $C_{1-6}$ alkoxy), benzyloxy, carboxy, aryl, and so forth.

Chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g., CH₃—CH₂—), in certain circumstances a bivalent linking moiety can be "alkyl," in which case those skilled in the art will understand the alkyl to be a divalent radical (e.g., —CH₂—CH₂—), which is equivalent to the term "alkylene." (Similarly, in circumstances in which a divalent moiety is required and is stated as being "aryl," those skilled in the art will understand that the term "aryl" refers to the corresponding multivalent moiety, arylene). All atoms are understood to have their normal number of valences for bond formation (i.e., 1 for H, 4 for carbon, 3 for N, 2 for O, and 2, 4, or 6 for S, depending on the oxidation state of the S).

"Pharmacologically effective amount," "physiologically effective amount," and "therapeutically effective amount" are used interchangeably herein to mean the amount of the compound of the invention present in a composition that is needed to provide a desired level of the compound (or desired metabolite thereof) the bloodstream or in the target tissue. The precise amount may depend upon numerous factors, e.g., the particular active agent, the components and physical characteristics of the composition, intended patient population, patient considerations, and may readily be determined by one skilled in the art, based upon the information provided herein and available in the relevant literature.

A "difunctional" oligomer is an oligomer having two functional groups contained therein, typically at its termini. When the functional groups are the same, the oligomer is said to be homodifunctional. When the functional groups are different, the oligomer is said to be heterodifunctional.

A basic reactant or an acidic reactant described herein include neutral, charged, and any corresponding salt forms thereof.

The term "patient," refers to a living organism suffering from or prone to a condition that can be prevented or treated by administration of a compound of the invention described herein, and includes both humans and animals.

"Optional" or "optionally" means that the subsequently described circumstance may but need not necessarily occur, so that the description includes instances where the circumstance occurs and instances where it does not.

As indicated above, the present invention is directed to (among other things) a compound comprising a substituted aromatic triazine residue covalently attached via a stable or degradable linkage to a water-soluble, non-peptidic oligomer. The "substituted aromatic triazine residue" is a compound having a structure of a substituted aromatic triazine moiety that is altered by the presence of one or more bonds, which bonds serve to attach (either directly or indirectly) one or more water-soluble, non-peptidic oligomers. Exemplary substituted aromatic triazine moieties have a structure encompassed by Formula I:

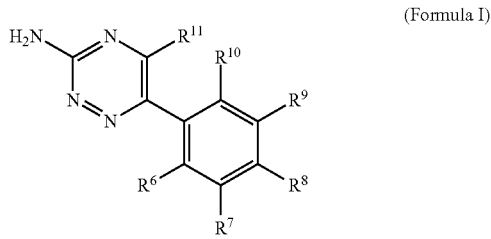

(Formula I)

wherein:

with respect to $R^6$ and $R^7$, either (i) $R^6$ is selected from the group consisting of halo, $C_{1-4}$ alkyl and trifluoromethyl (and preferably selected from the group consisting of chlorine, bromine, iodine, $C_{1-4}$ alkyl or trifluoromethyl, and more preferably is chlorine) and $R^7$ is selected from the group consisting of hydrogen, halo, $C_{1-4}$ alkyl and trifluoromethyl (and preferably selected from the group consisting of hydrogen, chloro and bromo), or (ii) $R^6$ and $R^7$ combine to form —CH═CH—CH═CH— optionally substituted by halo, $C_{1-4}$ alkyl or trifluoromethyl;

$R^8$ is selected from the group consisting of hydrogen, halo, $C_{1-4}$ alkyl and trifluoromethyl (and preferably selected from the group consisting of hydrogen, bromo, iodo, $C_{1-4}$ alkyl and trifluoromethyl, and more preferably selected from hydrogen and bromo);

$R^9$ is selected from the group consisting of hydrogen, halo, $C_{1-4}$ alkyl and trifluoromethyl (and preferably selected from the group consisting of hydrogen, chloro and bromo);

$R^{10}$ is selected from the group consisting of hydrogen, halo, $C_{1-4}$ alkyl and trifluoromethyl (and preferably selected from the group consisting of hydrogen, fluoro and methyl); and $R^{11}$ is selected from the group consisting of amino, $C_{1-10}$ acylamino and di-substituted aminomethyleneamino.

In one or more embodiments of the invention, a compound is provided, the compound comprising a substituted aromatic triazine residue covalently attached via a stable or degradable linkage to a water-soluble, non-peptidic oligomer, wherein the substituted aromatic triazine residue (in a form in which the water-soluble, non-peptidic oligomer is not present) is lamotrigine. The following list provides the chemical structure of lamotrigine and other exemplary substituted aromatic triazine moieties:

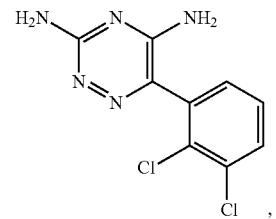

3,5-diamino-6-(2,3-dichlorophenyl)-1,2,4-triazine (also referred to as "lamotrigine");

3,5-diamino-6-(2,5-dichlorophenyl)-1,2,4-triazine;

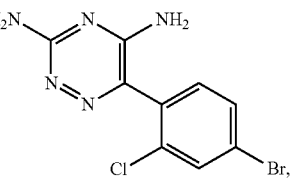

3,5-diamino-6-(4-bromo-2-chlorophenyl)-1,2,4-triazine;

-continued

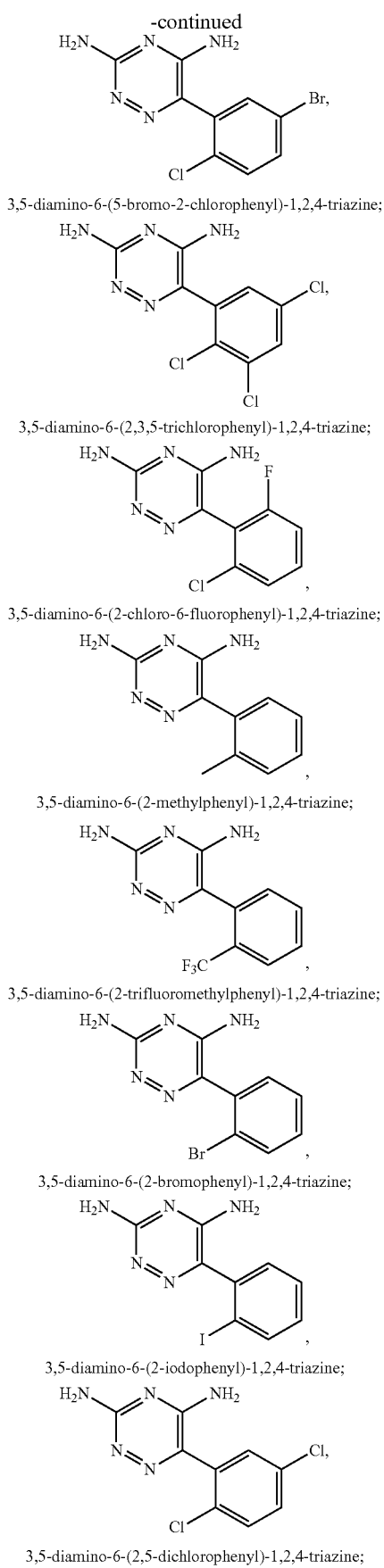

3,5-diamino-6-(5-bromo-2-chlorophenyl)-1,2,4-triazine;

3,5-diamino-6-(2,3,5-trichlorophenyl)-1,2,4-triazine;

3,5-diamino-6-(2-chloro-6-fluorophenyl)-1,2,4-triazine;

3,5-diamino-6-(2-methylphenyl)-1,2,4-triazine;

3,5-diamino-6-(2-trifluoromethylphenyl)-1,2,4-triazine;

3,5-diamino-6-(2-bromophenyl)-1,2,4-triazine;

3,5-diamino-6-(2-iodophenyl)-1,2,4-triazine;

3,5-diamino-6-(2,5-dichlorophenyl)-1,2,4-triazine;

-continued

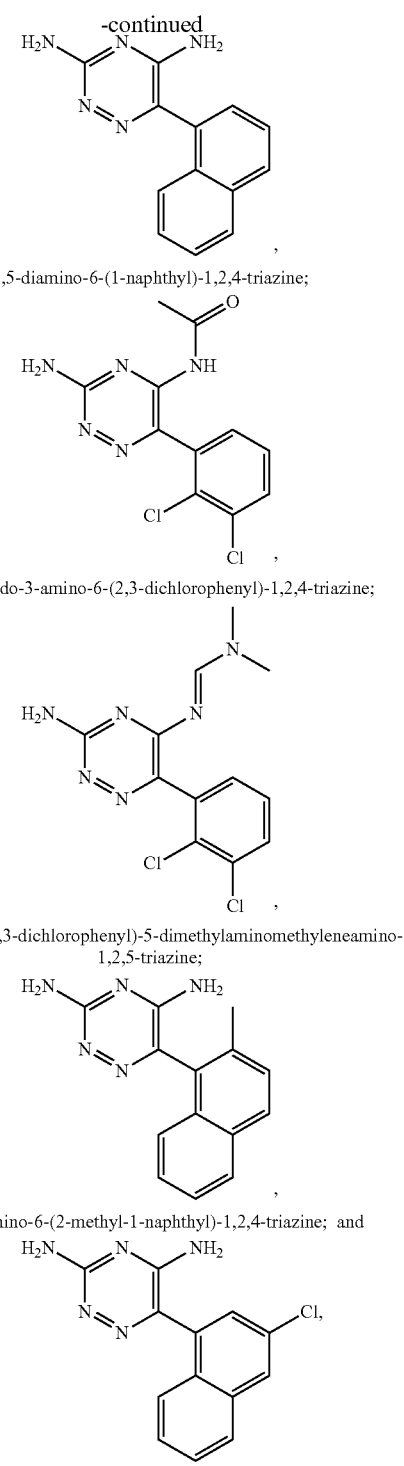

3,5-diamino-6-(1-naphthyl)-1,2,4-triazine;

5-acetamido-3-amino-6-(2,3-dichlorophenyl)-1,2,4-triazine;

3-amino-6-(2,3-dichlorophenyl)-5-dimethylaminomethyleneamino-1,2,5-triazine;

3,5-diamino-6-(2-methyl-1-naphthyl)-1,2,4-triazine; and 3,5-diamino-6-(3-chloro-1-naphthyl)-1,2,4-triazine.

In some instances, a substituted aromatic triazine moiety that is useful as a starting material or intermediate in synthesizing the compounds of the invention can be obtained from commercial sources. In addition, substituted aromatic triazine moieties can be obtained through chemical synthesis. Further examples of substituted aromatic triazine moieties, as well as synthetic approaches for preparing substituted aromatic triazine moieties, are described in the literature and in, for example, U.S. Pat. No. 4,602,017. Each of these (and other) substituted aromatic triazine moieties can be covalently attached (either directly or through one or more atoms) to a water-soluble, non-peptidic oligomer, following the techniques and approaches described herein.

Exemplary compounds of the invention include those having the following structure:

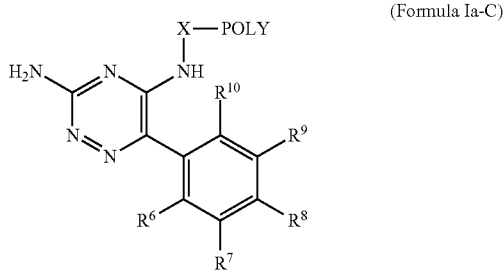

(Formula Ia-C)

wherein:

with respect to $R^6$ and $R^7$, either (i) $R^6$ is selected from the group consisting of halo, $C_{1-4}$ alkyl and trifluoromethyl (and preferably selected from the group consisting of chlorine, bromine, iodine, $C_{1-4}$ alkyl or trifluoromethyl, and more preferably is chlorine) and $R^7$ is selected from the group consisting of hydrogen, halo, $C_{1-4}$ alkyl and trifluoromethyl (and preferably selected from the group consisting of hydrogen, chloro and bromo), or (ii) $R^6$ and $R^7$ combine to form —CH═CH—CH═CH— optionally substituted by halo, $C_{1-4}$ alkyl or trifluoromethyl;

$R^8$ is selected from the group consisting of hydrogen, halo, $C_{1-4}$ alkyl and trifluoromethyl (and preferably selected from the group consisting of hydrogen, bromo, iodo, $C_{1-4}$ alkyl and trifluoromethyl, and more preferably selected from hydrogen and bromo);

$R^9$ is selected from the group consisting of hydrogen, halo, $C_{1-4}$ alkyl and trifluoromethyl (and preferably selected from the group consisting of hydrogen, chloro and bromo);

$R^{10}$ is selected from the group consisting of hydrogen, halo, $C_{1-4}$ alkyl and trifluoromethyl (and preferably selected from the group consisting of hydrogen, fluoro and methyl);

X is a spacer moiety; and

POLY is a water-soluble, non-peptidic oligomer.

Further exemplary compounds of the invention include those having the following structure:

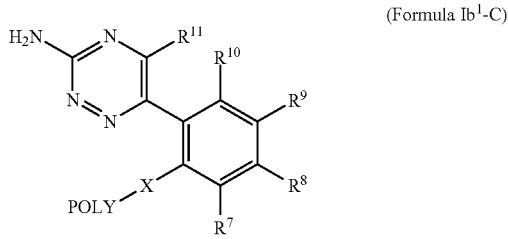

(Formula Ib¹-C)

wherein:

$R^7$ is selected from the group consisting of hydrogen, halo, $C_{1-4}$ alkyl and trifluoromethyl (and preferably selected from the group consisting of hydrogen, chloro and bromo);

$R^8$ is selected from the group consisting of hydrogen, halo, $C_{1-4}$ alkyl and trifluoromethyl (and preferably selected from the group consisting of hydrogen, bromo, iodo, $C_{1-4}$ alkyl and trifluoromethyl, and more preferably selected from hydrogen and bromo);

$R^9$ is selected from the group consisting of hydrogen, halo, $C_{1-4}$ alkyl and trifluoromethyl (and preferably selected from the group consisting of hydrogen, chloro and bromo);

$R^{10}$ is selected from the group consisting of hydrogen, halo, $C_{1-4}$ alkyl and trifluoromethyl (and preferably selected from the group consisting of hydrogen, fluoro and methyl);

$R^{11}$ is selected from the group consisting of amino, $C_{1-10}$ acylamino and di-substituted aminomethyleneamino;

X is a spacer moiety; and

POLY is a water-soluble, non-peptidic oligomer.

Still further exemplary compounds of the invention include those having the following structure:

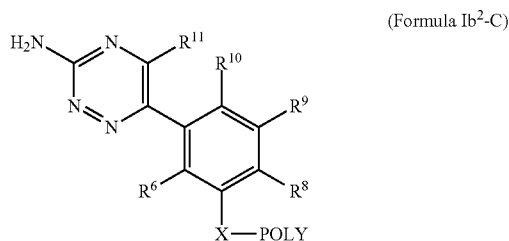

(Formula Ib²-C)

wherein:

$R^6$ is selected from the group consisting of halo, $C_{1-4}$ alkyl and trifluoromethyl (and preferably selected from the group consisting of chlorine, bromine, iodine, $C_{1-4}$ alkyl or trifluoromethyl, and more preferably is chlorine);

$R^8$ is selected from the group consisting of hydrogen, halo, $C_{1-4}$ alkyl and trifluoromethyl (and preferably selected from the group consisting of hydrogen, bromo, iodo, $C_{1-4}$ alkyl and trifluoromethyl, and more preferably selected from hydrogen and bromo);

$R^9$ is selected from the group consisting of hydrogen, halo, $C_{1-4}$ alkyl and trifluoromethyl (and preferably selected from the group consisting of hydrogen, chloro and bromo);

$R^{10}$ is selected from the group consisting of hydrogen, halo, $C_{1-4}$ alkyl and trifluoromethyl (and preferably selected from the group consisting of hydrogen, fluoro and methyl);

$R^{11}$ is selected from the group consisting of amino, $C_{1-10}$ acylamino and di-substituted aminomethyleneamino;

X is a spacer moiety; and

POLY is a water-soluble, non-peptidic oligomer.

Still further exemplary compounds of the invention include those having the following structure:

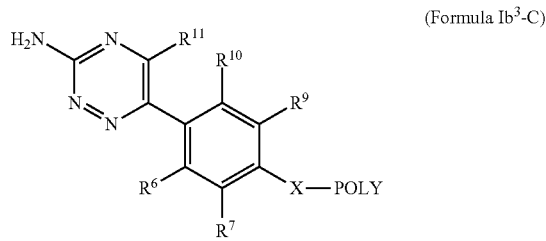

(Formula Ib³-C)

wherein:

with respect to $R^6$ and $R^7$, either (i) $R^6$ is selected from the group consisting of halo, $C_{1-4}$ alkyl and trifluoromethyl (and preferably selected from the group consisting of chlorine, bromine, iodine, $C_{1-4}$ alkyl or trifluoromethyl, and more preferably is chlorine) and $R^7$ is selected from the group consisting of hydrogen, halo, $C_{1-4}$ alkyl and trifluoromethyl (and preferably selected from the group consisting of hydrogen, chloro and bromo), or (ii) $R^6$ and $R^7$ combine to form —CH═CH—CH═CH— optionally substituted by halo, $C_{1-4}$ alkyl or trifluoromethyl;

$R^9$ is selected from the group consisting of hydrogen, halo, $C_{1-4}$ alkyl and trifluoromethyl (and preferably selected from the group consisting of hydrogen, chloro and bromo);

$R^{10}$ is selected from the group consisting of hydrogen, halo, $C_{1-4}$ alkyl and trifluoromethyl (and preferably selected from the group consisting of hydrogen, fluoro and methyl);

$R^{11}$ is selected from the group consisting of amino, $C_{1-10}$ acylamino and di-substituted aminomethyleneamino;

X is a spacer moiety; and

POLY is a water-soluble, non-peptidic oligomer.

Use of discrete oligomers (e.g., from a monodisperse or bimodal composition of oligomers, in contrast to relatively impure compositions) to form oligomer-containing compounds are preferred. For instance, a compound of the invention, when administered by any of a number of suitable administration routes, such as parenteral, oral, transdermal, buccal, pulmonary, or nasal, exhibits reduced penetration across the blood-brain barrier. It is preferred that the compounds of the invention exhibit slowed, minimal or effectively no crossing of the blood-brain barrier, while still crossing the gastro-intestinal (GI) walls and into the systemic circulation if oral delivery is intended. Moreover, the compounds of the invention maintain a degree of bioactivity as well as bioavailability in comparison to the bioactivity and bioavailability of the compound free of all oligomers.

With respect to the blood-brain barrier ("BBB"), this barrier restricts the transport of drugs from the blood to the brain. This barrier consists of a continuous layer of unique endothelial cells joined by tight junctions. The cerebral capillaries, which comprise more than 95% of the total surface area of the BBB, represent the principal route for the entry of most solutes and drugs into the central nervous system.

For compounds whose degree of blood-brain barrier crossing ability is not readily known, such ability may be determined using a suitable animal model such as an in situ rat brain perfusion ("RBP") model as described herein. Briefly, the RBP technique involves cannulation of the carotid artery followed by perfusion with a compound solution under controlled conditions, followed by a wash out phase to remove compound remaining in the vascular space. (Such analyses may be conducted, for example, by contract research organizations such as Absorption Systems, Exton, Pa.). In one example of the RBP model, a cannula is placed in the left carotid artery and the side branches are tied off. A physiologic buffer containing the analyte (typically but not necessarily at a 5 micromolar concentration level) is perfused at a flow rate of about 10 mL/minute in a single pass perfusion experiment. After 30 seconds, the perfusion is stopped and the brain vascular contents are washed out with compound-free buffer for an additional 30 seconds. The brain tissue is then removed and analyzed for compound concentrations via liquid chromatography with tandem mass spectrometry detection (LC/MS/MS). Alternatively, blood-brain barrier permeability can be estimated based upon a calculation of the compound's molecular polar surface area ("PSA"), which is defined as the sum of surface contributions of polar atoms (usually oxygens, nitrogens and attached hydrogens) in a molecule. The PSA has been shown to correlate with compound transport properties such as blood-brain barrier transport. Methods for determining a compound's PSA can be found, e.g., Ertl et al. (2000) *J. Med. Chem.* 43:3714-3717 and Kelder et al. (1999) *Pharm. Res.* 16:1514-1519.

With respect to the blood-brain barrier, the water-soluble, non-peptidic oligomer-containing compound of the invention exhibits a blood-brain barrier crossing rate that is reduced as compared to the crossing rate of the small molecule drug not attached to the water-soluble, non-peptidic oligomer. Exemplary reductions in blood-brain barrier crossing rates for the compounds described herein include reductions of: at least about 5%; at least about 10%; at least about 25%; at least about 30%; at least about 40%; at least about 50%; at least about 60%; at least about 70%; at least about 80%; or at least about 90%, when compared to the blood-brain barrier crossing rate of the corresponding compound lacking water-soluble, non-peptidic oligomer(s). A preferred reduction in the blood-brain barrier crossing rate for a conjugate of the invention is at least about 20%.

Assays for determining whether a given compound (regardless of whether the compound includes a water-soluble, non-peptidic oligomer or not) can act as a substituted aromatic triazine moiety are known and/or may be prepared by one of ordinary skill in the art and are further described infra.

Briefly, one approach for testing whether a given substituted aromatic triazine moiety has anticonvulsant activity (as evidenced through a maximal electroshock test) is described in L. A. Woodbury and V. D. Davenport (1952) *Design and Use of a New Electroshock Seizure Apparatus, and Analysis of Factors Altering Seizure Threshold and Pattern Arch Int Pharmacodyn Ther* 92:97-104.

Each of these (and other) substituted aromatic triazine moieties can be covalently attached (either directly or through one or more atoms) to a water-soluble, non-peptidic oligomer.

Exemplary molecular weights of a small molecule substituted aromatic triazine moiety (prior to, for example, conjugation to a water-soluble, non-peptidic oligomer) include molecular weights of: less than about 950; less than about 900; less than about 850; less than about 800; less than about 750; less than about 700; less than about 650; less than about 600; less than about 550; less than about 500; less than about 450; less than about 400; less than about 350; and less than about 300 Daltons.

The small molecule drug used in the invention, if chiral, may be obtained from a racemic mixture, or an optically active form, for example, a single optically active enantiomer, or any combination or ratio of enantiomers (e.g., scalemic and racemic mixtures). In addition, the small molecule drug may possess one or more geometric isomers. With respect to geometric isomers, a composition can comprise a single geometric isomer or a mixture of two or more geometric isomers. A small molecule drug for use in the present invention can be in its customary active form, or may possess some degree of modification. For example, a small molecule drug may have a targeting agent, tag, or transporter attached thereto, prior to or after covalent attachment of an oligomer. Alternatively, the small molecule drug may possess a lipophilic moiety attached thereto, such as a phospholipid (e.g., distearoylphosphatidylethanolamine or "DSPE," dipalmitoylphosphatidylethanolamine or "DPPE," and so forth) or a small fatty acid. In some instances, however, it is preferred that the small molecule drug moiety does not include attachment to a lipophilic moiety.

The substituted aromatic triazine moiety for coupling to a water-soluble, non-peptidic oligomer possesses a free hydroxyl, carboxyl, thio, amino group, or the like (i.e., "handle") suitable for covalent attachment to the oligomer. In addition, the substituted aromatic triazine moiety may be modified by introduction of a reactive group, preferably by conversion of one of its existing functional groups to a functional group suitable for formation of a stable covalent linkage between the oligomer and the drug.

Each oligomer is composed of up to three different monomer types selected from the group consisting of: alkylene oxide, such as ethylene oxide or propylene oxide; olefinic alcohol, such as vinyl alcohol, 1-propenol or 2-propenol; vinyl pyrrolidone; hydroxyalkyl methacrylamide or hydroxyalkyl methacrylate, where alkyl is preferably methyl; α-hydroxy acid, such as lactic acid or glycolic acid; phosphazene, oxazoline, amino acids, carbohydrates such as monosaccharides, alditol such as mannitol; and N-acryloylmorpholine. Preferred monomer types include alkylene oxide, olefinic alcohol, hydroxyalkyl methacrylamide or methacrylate, N-acryloylmorpholine, and α-hydroxy acid. Preferably, each oligomer is, independently, a co-oligomer of two monomer types selected from this group, or, more preferably, is a homo-oligomer of one monomer type selected from this group.

The two monomer types in a co-oligomer may be of the same monomer type, for example, two alkylene oxides, such as ethylene oxide and propylene oxide. Preferably, the oligomer is a homo-oligomer of ethylene oxide. Usually, although not necessarily, the terminus (or termini) of the oligomer that is not covalently attached to a small molecule is capped to render it unreactive. Alternatively, the terminus may include a reactive group. When the terminus is a reactive group, the reactive group is either selected such that it is unreactive under the conditions of formation of the final oligomer or during covalent attachment of the oligomer to a small molecule drug, or it is protected as necessary. One common end-functional group is hydroxyl or —OH, particularly for oligoethylene oxides.

The water-soluble, non-peptidic oligomer (e.g., "POLY" in various structures provided herein) can have any of a number of different geometries. For example, the water-soluble, non-peptidic oligomer can be linear, branched, or forked. Most typically, the water-soluble, non-peptidic oligomer is linear or is branched, for example, having one branch point. Although much of the discussion herein is focused upon poly(ethylene oxide) as an illustrative oligomer, the discussion and structures presented herein can be readily extended to encompass any water-soluble, non-peptidic oligomers described above.

The molecular weight of the water-soluble, non-peptidic oligomer, excluding the linker portion, is generally relatively low. Exemplary values of the molecular weight of the water-soluble polymer include: below about 1500; below about 1450; below about 1400; below about 1350; below about 1300; below about 1250; below about 1200; below about 1150; below about 1100; below about 1050; below about 1000; below about 950; below about 900; below about 850; below about 800; below about 750; below about 700; below about 650; below about 600; below about 550; below about 500; below about 450; below about 400; below about 350; below about 300; below about 250; below about 200; and below about 100 Daltons.

Exemplary ranges of molecular weights of the water-soluble, non-peptidic oligomer (excluding the linker) include: from about 100 to about 1400 Daltons; from about 100 to about 1200 Daltons; from about 100 to about 800 Daltons; from about 100 to about 500 Daltons; from about 100 to about 400 Daltons; from about 200 to about 500 Daltons; from about 200 to about 400 Daltons; from about 75 to 1000 Daltons; and from about 75 to about 750 Daltons.

Preferably, the number of monomers in the water-soluble, non-peptidic oligomer falls within one or more of the following ranges: between about 1 and about 30 (inclusive); between about 1 and about 25; between about 1 and about 20; between about 1 and about 15; between about 1 and about 12; between about 1 and about 10. In certain instances, the number of monomers in series in the oligomer (and the corresponding conjugate) is one of 1, 2, 3, 4, 5, 6, 7, or 8. In additional embodiments, the oligomer (and the corresponding conjugate) contains 9, 10, 11, 12, 13, 14, 15, 16, 17, 18, 19, or 20 monomers. In yet further embodiments, the oligomer (and the corresponding conjugate) possesses 21, 22, 23, 24, 25, 26, 27, 28, 29 or 30 monomers in series. Thus, for example, when the water-soluble, non-peptidic polymer includes $CH_3—(OCH_2CH_2)_n—$, "n" is an integer that can be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, and can fall within one or more of the following ranges: between about 1 and about 25; between about 1 and about 20; between about 1 and about 15; between about 1 and about 12; between about 1 and about 10.

When the water-soluble, non-peptidic oligomer has 1, 2, 3, 4, 5, 6, 7, 8, 9, or 10 monomers, these values correspond to a methoxy end-capped oligo(ethylene oxide) having a molecular weights of about 75, 119, 163, 207, 251, 295, 339, 383, 427, and 471 Daltons, respectively. When the oligomer has 11, 12, 13, 14, or 15 monomers, these values correspond to methoxy end-capped oligo(ethylene oxide) having molecular weights corresponding to about 515, 559, 603, 647, and 691 Daltons, respectively.

When the water-soluble, non-peptidic oligomer is attached to the substituted aromatic triazine moiety (in contrast to the step-wise addition of one or more monomers to effectively "grow" the oligomer onto the substituted aromatic triazine), it is preferred that the composition containing an activated form of the water-soluble, non-peptidic oligomer be monodisperse. In those instances, however, where a bimodal composition is employed, the composition will possess a bimodal distribution centering around any two of the above numbers of monomers. For instance, a bimodal oligomer may have any one of the following exemplary combinations of monomer subunits: 1-2, 1-3, 1-4, 1-5, 1-6, 1-7, 1-8, 1-9, 1-10, and so forth; 2-3, 2-4, 2-5, 2-6, 2-7, 2-8, 2-9, 2-10, and so forth; 3-4, 3-5, 3-6, 3-7, 3-8, 3-9, 3-10, and so forth; 4-5, 4-6, 4-7, 4-8, 4-9, 4-10, and so forth; 5-6, 5-7, 5-8, 5-9, 5-10, and so forth; 6-7, 6-8, 6-9, 6-10, and so forth; 7-8, 7-9, 7-10, and so forth; and 8-9, 8-10, and so forth.

In some instances, the composition containing an activated form of the water-soluble, non-peptidic oligomer will be trimodal or even tetramodal, possessing a range of monomers units as previously described. Oligomer compositions possessing a well-defined mixture of oligomers (i.e., being bimodal, trimodal, tetramodal, and so forth) can be prepared by mixing purified monodisperse oligomers to obtain a desired profile of oligomers (a mixture of two oligomers differing only in the number of monomers is bimodal; a mixture of three oligomers differing only in the number of monomers is trimodal; a mixture of four oligomers differing only in the number of monomers is tetramodal), or alternatively, can be obtained from column chromatography of a polydisperse oligomer by recovering the "center cut", to obtain a mixture of oligomers in a desired and defined molecular weight range.

It is preferred that the water-soluble, non-peptidic oligomer is obtained from a composition that is preferably unimolecular or monodisperse. That is, the oligomers in the composition possess the same discrete molecular weight value rather than a distribution of molecular weights. Some monodisperse oligomers can be purchased from commercial sources such as those available from Sigma-Aldrich, or alternatively, can be prepared directly from commercially available starting materials such as Sigma-Aldrich. Water-soluble, non-peptidic oligomers can be prepared as described in Chen Y., Baker, G. L., *J. Org. Chem.*, 6870-6873 (1999), WO 02/098949, and U.S. Patent Application Publication No. 2005/0136031.

The spacer moiety (the linker through which the water-soluble, non-peptidic polymer is attached to the substituted aromatic triazine moiety) may be a single bond, a single atom, such as an oxygen atom or a sulfur atom, two atoms, or a number of atoms. A spacer moiety is typically but is not necessarily linear in nature. The spacer moiety, "X," is hydrolytically stable, and is preferably also enzymatically stable. Preferably, the spacer moiety "X" is one having a chain length of less than about 12 atoms, and preferably less than about 10 atoms, and even more preferably less than about 8 atoms and even more preferably less than about 5 atoms, whereby length is meant the number of atoms in a single chain, not counting substituents. For instance, a urea linkage such as this, $R_{oligomer}$—NH—(C=O)—NH—$R'_{drug}$, is considered to have a chain length of 3 atoms (—NH—C(O)—NH—). In selected embodiments, the linkage does not comprise further spacer groups.

In some instances, the spacer moiety "X" comprises an ether, amide, urethane, amine, thioether, urea, or a carbon-carbon bond. Functional groups such as those discussed below, and illustrated in the examples, are typically used for forming the linkages. The spacer moiety may less preferably also comprise (or be adjacent to or flanked by) other atoms, as described further below.

More specifically, in selected embodiments, a spacer moiety, "X," may be any of the following: "—" (i.e., a covalent bond, that may be stable or degradable, between the substituted aromatic triazine residue and the water-soluble, non-peptidic oligomer), —O—, —NH—, —S—, —C(O)—, —C(O)O—, —OC(O)—, —CH$_2$—C(O)O—, —CH$_2$—OC(O)—, —C(O)O—CH$_2$—, —OC(O)—CH$_2$—, C(O)—NH, NH—C(O)—NH, O—C(O)—NH, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$, —CH$_2$—CH$_2$—NH—C(O)—CH$_2$—CH$_2$, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, bivalent cycloalkyl group, —N($R^6$)—, $R^6$ is H or an organic radical selected from the group consisting of alkyl, substituted alkyl, alkenyl, substituted alkenyl, alkynyl, substituted alkynyl, aryl and substituted aryl. Additional spacer moieties include, acylamino, acyl, aryloxy, alkylene bridge containing between 1 and 5 inclusive carbon atoms, alkylamino, dialkylamino having about 2 to 4 inclusive carbon atoms, piperidino, pyrrolidino, N-(lower alkyl)-2-piperidyl, morpholino, 1-piperizinyl, 4-(lower alkyl)-1-piperizinyl, 4-(hydroxyl-lower alkyl)-1-piperizinyl, 4-(methoxy-lower alkyl)-1-piperizinyl, and guanidine. In some instances, a portion or a functional group of the drug compound may be modified or removed altogether to facilitate attachment of the oligomer. In some instances, it is preferred that X is not an amide, i.e., —CONR— and —RNCO—).

For purposes of the present invention, however, a group of atoms is not considered a linkage when it is immediately adjacent to an oligomer segment, and the group of atoms is the same as a monomer of the oligomer such that the group would represent a mere extension of the oligomer chain.

The spacer moiety "X" between the water-soluble, non-peptidic oligomer and the small molecule is formed by reaction of a functional group on a terminus of the oligomer (or nascent oligomer when it is desired to "grow" the oligomer onto the substituted aromatic triazine) with a corresponding functional group within the substituted aromatic triazine. Illustrative reactions are described briefly below. For example, an amino group on an oligomer may be reacted with a carboxylic acid or an activated carboxylic acid derivative on the small molecule, or vice versa, to produce an amide linkage. Alternatively, reaction of an amine on an oligomer with an activated carbonate (e.g., succinimidyl or benzotriazolyl carbonate) on the drug, or vice versa, forms a carbamate linkage. Reaction of an amine on an oligomer with an isocyanate (R—N=C=O) on a drug, or vice versa, forms a urea linkage (R—NH—(C=O)—NH—R'). Further, reaction of an alcohol (alkoxide) group on an oligomer with an alkyl halide, or halide group within a drug, or vice versa, forms an ether linkage. In yet another coupling approach, a small molecule having an aldehyde function is coupled to an oligomer amino group by reductive amination, resulting in formation of a secondary amine linkage between the oligomer and the small molecule.

A particularly preferred water-soluble, non-peptidic oligomer is an oligomer bearing an aldehyde functional group. In this regard, the oligomer will have the following structure: CH$_3$O—(CH$_2$—CH$_2$—O)$_n$—(CH$_2$)$_p$—C(O)H, wherein (n) is one of 1, 2, 3, 4, 5, 6, 7, 8, 9 and 10 and (p) is one of 1, 2, 3, 4, 5, 6 and 7. Preferred (n) values include 3, 5 and 7 and preferred (p) values 2, 3 and 4.

The termini of the water-soluble, non-peptidic oligomer not bearing a functional group may be capped to render it unreactive. When the oligomer includes a further functional group at a terminus other than that intended for formation of a conjugate, that group is either selected such that it is unreactive under the conditions of formation of the spacer moiety (e.g., "X") or it is protected during the formation of the spacer moiety (e.g., "X").

As stated above, the water-soluble, non-peptidic oligomer includes at least one functional group prior to conjugation. The functional group comprises an electrophilic or nucleophilic group for covalent attachment to a small molecule, depending upon the reactive group contained within or introduced into the small molecule. Examples of nucleophilic groups that may be present in either the oligomer or the small molecule include hydroxyl, amine, hydrazine (—NHNH$_2$), hydrazide (—C(O)NHNH$_2$), and thiol. Preferred nucleophiles include amine, hydrazine, hydrazide, and thiol, particularly amine. Most small molecule drugs for covalent attachment to an oligomer will possess a free hydroxyl, amino, thio, aldehyde, ketone, or carboxyl group.

Examples of electrophilic functional groups that may be present in either the oligomer or the small molecule include carboxylic acid, carboxylic ester, particularly imide esters, orthoester, carbonate, isocyanate, isothiocyanate, aldehyde, ketone, thione, alkenyl, acrylate, methacrylate, acrylamide, sulfone, maleimide, disulfide, iodo, epoxy, sulfonate, thiosulfonate, silane, alkoxysilane, and halosilane. More specific examples of these groups include succinimidyl ester or carbonate, imidazoyl ester or carbonate, benzotriazole ester or carbonate, vinyl sulfone, chloroethylsulfone, vinylpyridine, pyridyl disulfide, iodoacetamide, glyoxal, dione, mesylate, tosylate, and tresylate (2,2,2-trifluoroethanesulfonate).

Also included are sulfur analogs of several of these groups, such as thione, thione hydrate, thioketal, 2-thiazolidine thione, etc., as well as hydrates or protected derivatives of any of the above moieties (e.g., aldehyde hydrate, hemiacetal, acetal, ketone hydrate, hemiketal, ketal, thioketal, thioacetal).

An "activated derivative" of a carboxylic acid refers to a carboxylic acid derivative that reacts readily with nucleophiles, generally much more readily than the underivatized carboxylic acid. Activated carboxylic acids include, for example, acid halides (such as acid chlorides), anhydrides, carbonates, and esters. Such esters include imide esters, of the general form —(CO)O—N[(CO)—]$_2$; for example, N-hydroxysuccinimidyl (NHS) esters or N-hydroxyphthalimidyl esters. Also preferred are imidazolyl esters and benzotriazole esters. Particularly preferred are activated propionic acid or butanoic acid esters, as described in co-owned U.S. Pat. No. 5,672,662. These include groups of the form —(CH$_2$)$_{2-3}$C(=O)O-Q, where Q is preferably selected from N-succinimide, N-sulfosuccinimide, N-phthalimide, N-glutarimide, N-tetrahydrophthalimide, N-norbornene-2,3-dicarboximide, benzotriazole, 7-azabenzotriazole, and imidazole.

Other preferred electrophilic groups include succinimidyl carbonate, maleimide, benzotriazole carbonate, glycidyl ether, imidazoyl carbonate, p-nitrophenyl carbonate, acrylate, tresylate, aldehyde, and orthopyridyl disulfide.

These electrophilic groups are subject to reaction with nucleophiles, e.g., hydroxy, thio, or amino groups, to produce various bond types. Preferred for the present invention are reactions which favor formation of a hydrolytically stable linkage. For example, carboxylic acids and activated derivatives thereof, which include orthoesters, succinimidyl esters, imidazolyl esters, and benzotriazole esters, react with the above types of nucleophiles to form esters, thioesters, and amides, respectively, of which amides are the most hydrolytically stable. Carbonates, including succinimidyl, imidazolyl, and benzotriazole carbonates, react with amino groups to form carbamates. Isocyanates (R—N—C=O) react with hydroxyl or amino groups to form, respectively, carbamate (RNH—C(O)—OR') or urea (RNH—C(O)—NHR') linkages. Aldehydes, ketones, glyoxals, diones and their hydrates or alcohol adducts (i.e., aldehyde hydrate, hemiacetal, acetal, ketone hydrate, hemiketal, and ketal) are preferably reacted with amines, followed by reduction of the resulting imine, if desired, to provide an amine linkage (reductive amination).

Several of the electrophilic functional groups include electrophilic double bonds to which nucleophilic groups, such as thiols, can be added, to form, for example, thioether bonds. These groups include maleimides, vinyl sulfones, vinyl pyridine, acrylates, methacrylates, and acrylamides. Other groups comprise leaving groups that can be displaced by a nucleophile; these include chloroethyl sulfone, pyridyl disulfides (which include a cleavable S—S bond), iodoacetamide, mesylate, tosylate, thiosulfonate, and tresylate. Epoxides react by ring opening by a nucleophile, to form, for example, an ether or amine bond. Reactions involving complementary reactive groups such as those noted above on the oligomer and the small molecule are utilized to prepare the conjugates of the invention.

In some instances the substituted aromatic triazine moiety may not have a functional group suited for conjugation. In this instance, it is possible to modify (or "functionalize") the "original" substituted aromatic triazine moiety so that it does have a functional group suited for conjugation. For example, if the substituted aromatic triazine moiety has an amide group, but an amine group is desired, it is possible to modify the amide group to an amine group by way of a Hofmann rearrangement, Curtius rearrangement (once the amide is converted to an azide) or Lossen rearrangement (once amide is concerted to hydroxamide followed by treatment with toluene-2-sulfonyl chloride/base).

It is possible to prepare a conjugate of a substituted aromatic triazine moiety bearing a carboxyl group wherein the carboxyl group-bearing substituted aromatic triazine moiety is coupled to an amino-terminated oligomeric ethylene glycol, to provide a conjugate having an amide group covalently linking the substituted aromatic triazine moiety to the oligomer. This can be performed, for example, by combining the carboxyl group-bearing substituted aromatic triazine moiety with the amino-terminated oligomeric ethylene glycol in the presence of a coupling reagent, (such as dicyclohexylcarbodiimide or "DCC") in an anhydrous organic solvent.

Further, it is possible to prepare a conjugate of a substituted aromatic triazine moiety bearing a hydroxyl group wherein the hydroxyl group-bearing substituted aromatic triazine moiety is coupled to an oligomeric ethylene glycol halide to result in an ether (—O—) linked conjugate. This can be performed, for example, by using sodium hydride to deprotonate the hydroxyl group followed by reaction with a halide-terminated oligomeric ethylene glycol.

Further, it is possible to prepare a conjugate of a substituted aromatic triazine moiety bearing a hydroxyl group wherein the hydroxyl group-bearing substituted aromatic triazine moiety is coupled to an oligomeric ethylene glycol bearing an haloformate group [e.g., CH$_3$(OCH$_2$CH$_2$)$_n$OC(O)-halo, where halo is chloro, bromo, iodo] to result in a carbonate [—O—C(O)—O—] linked conjugate. This can be performed, for example, by combining a substituted aromatic triazine moiety and an oligomeric ethylene glycol bearing a haloformate group in the presence of a nucleophilic catalyst (such as 4-dimethylaminopyridine or "DMAP") to thereby result in the corresponding carbonate-linked conjugate.

In another example, it is possible to prepare a conjugate of a substituted aromatic triazine moiety bearing a ketone group by first reducing the ketone group to form the corresponding hydroxyl group. Thereafter, the substituted aromatic triazine moiety now bearing a hydroxyl group can be coupled as described herein.

In still another instance, it is possible to prepare a conjugate of a substituted aromatic triazine moiety bearing an amine group. In one approach, the amine group-bearing substituted aromatic triazine moiety and an aldehyde-bearing oligomer are dissolved in a suitable buffer after which a suitable reducing agent (e.g., NaCNBH$_3$) is added. Following reduction, the result is an amine linkage formed between the amine group of the amine group-containing substituted aromatic triazine moiety and the carbonyl carbon of the aldehyde-bearing oligomer.

In another approach for preparing a conjugate of a substituted aromatic triazine moiety bearing an amine group, a carboxylic acid-bearing oligomer and the amine group-bearing substituted aromatic triazine moiety are combined, in the presence of a coupling reagent (e.g., DCC). The result is an amide linkage formed between the amine group of the amine group-containing substituted aromatic triazine moiety and the carbonyl of the carboxylic acid-bearing oligomer.

While it is believed that the full scope of the compounds disclosed herein behave as described, an optimally sized oligomer can be identified as follows.

First, an oligomer obtained from a monodisperse or bimodal water soluble oligomer is conjugated to the substituted aromatic triazine moiety. Preferably, the drug is orally bioavailable, and on its own, exhibits a non-negligible blood-brain barrier crossing rate. Next, the ability of the conjugate to cross the blood-brain barrier is determined using an appropriate model and compared to that of the unmodified parent drug. If the results are favorable, that is to say, if, for example, the rate of crossing is significantly reduced, then the bioactivity of conjugate is further evaluated. Preferably, the compounds according to the invention maintain a significant degree of bioactivity relative to the parent drug, i.e., greater than about 30% of the bioactivity of the parent drug, or even more preferably, greater than about 50% of the bioactivity of the parent drug.

The above steps are repeated one or more times using oligomers of the same monomer type but having a different number of subunits and the results compared.

For each conjugate whose ability to cross the blood-brain barrier is reduced in comparison to the non-conjugated small molecule drug, its oral bioavailability is then assessed. Based upon these results, that is to say, based upon the comparison of conjugates of oligomers of varying size to a given small molecule at a given position or location within the small molecule, it is possible to determine the size of the oligomer most effective in providing a conjugate having an optimal balance between reduction in biological membrane crossing, oral bioavailability, and bioactivity. The small size of the oligomers makes such screenings feasible and allows one to effectively tailor the properties of the resulting conjugate. By making small, incremental changes in oligomer size and utilizing an experimental design approach, one can effectively identify a conjugate having a favorable balance of reduction in biological membrane crossing rate, bioactivity, and oral bioavailability. In some instances, attachment of an oligomer as described herein is effective to actually increase oral bioavailability of the drug.

For example, one of ordinary skill in the art, using routine experimentation, can determine a best suited molecular size and linkage for improving oral bioavailability by first preparing a series of oligomers with different weights and functional groups and then obtaining the necessary clearance profiles by administering the conjugates to a patient and taking periodic blood and/or urine sampling. Once a series of clearance profiles have been obtained for each tested conjugate, a suitable conjugate can be identified.

Animal models (rodents and dogs) can also be used to study oral drug transport. In addition, non-in vivo methods include rodent everted gut excised tissue and Caco-2 cell monolayer tissue-culture models. These models are useful in predicting oral drug bioavailability.

To determine whether the substituted aromatic triazine moiety or a compound of the invention (e.g., a conjugate of a substituted aromatic triazine moiety and a water-soluble non-peptidic oligomer) has activity as a substituted aromatic triazine moiety therapeutic, it is possible to test such a compound. The compound of interest may be tested using in vitro binding studies to receptors using various cell lines expressing these receptors that have become routine in pharmaceutical industry and described herein.

The compounds of the invention may be administered per se or in the form of a pharmaceutically acceptable salt, and any reference to the compounds of the invention herein is intended to include pharmaceutically acceptable salts. If used, a salt of a compound as described herein should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts can be prepared by reaction of the compound with an organic or inorganic acid, using standard methods detailed in the literature. Examples of useful salts include, but are not limited to, those prepared from the following acids: hydrochloric, hydrobromic, sulfuric, nitric, phosphoric, maleic, acetic, salicyclic, p-toluenesulfonic, tartaric, citric, methanesulfonic, formic, malonic, succinic, naphthalene-2-sulphonic and benzenesulphonic, and the like. Also, pharmaceutically acceptable salts can be prepared as alkaline metal or alkaline earth salts, such as sodium, potassium, or calcium salts of a carboxylic acid group.

The present invention also includes pharmaceutical preparations comprising a compound as provided herein in combination with a pharmaceutical excipient. Generally, the compound itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, maltitol, lactitol, xylitol, sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfate, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines, fatty acids and fatty esters; steroids, such as cholesterol; and chelating agents, such as EDTA, zinc and other such suitable cations.

Pharmaceutically acceptable acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the compound of the invention will vary depending on a number of factors, but will optimally be a therapeutically effective dose when the composition is stored in a unit dose container. A therapeutically effective dose can be determined experimentally by repeated administration of increasing amounts of the compound in order to determine which amount produces a clinically desired endpoint.

The amount of any individual excipient in the composition will vary depending on the activity of the excipient and particular needs of the composition. The optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, excipients will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients and general teachings regarding pharmaceutical compositions are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

The pharmaceutical compositions can take any number of forms and the invention is not limited in this regard. Exemplary preparations are most preferably in a form suitable for oral administration such as a tablet, caplet, capsule, gel cap, troche, dispersion, suspension, solution, elixir, syrup, lozenge, transdermal patch, spray, suppository, and powder.

Oral dosage forms are preferred for those conjugates that are orally active, and include tablets, caplets, capsules, gel caps, suspensions, solutions, elixirs, and syrups, and can also comprise a plurality of granules, beads, powders or pellets that are optionally encapsulated. Such dosage forms are prepared using conventional methods known to those in the field of pharmaceutical formulation and described in the pertinent texts.

Tablets and caplets, for example, can be manufactured using standard tablet processing procedures and equipment. Direct compression and granulation techniques are preferred when preparing tablets or caplets containing the conjugates described herein. In addition to the conjugate, the tablets and caplets will generally contain inactive, pharmaceutically acceptable carrier materials such as binders, lubricants, disintegrants, fillers, stabilizers, surfactants, coloring agents, flow agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethylcellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the conjugate-containing composition can be encapsulated in the form of a liquid or gel (e.g., in the case of a gel cap) or solid (including particulates such as granules, beads, powders or pellets). Suitable capsules include hard and soft capsules, and are generally made of gelatin, starch, or a cellulosic material. Two-piece hard gelatin capsules are preferably sealed, such as with gelatin bands or the like.

Included are parenteral formulations in the substantially dry form (as a lyophilizate or precipitate, which can be in the form of a powder or cake), as well as formulations prepared for injection, which are liquid and require the step of reconstituting the dry form of parenteral formulation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof.

In some cases, compositions intended for parenteral administration can take the form of nonaqueous solutions, suspensions, or emulsions, normally being sterile. Examples of nonaqueous solvents or vehicles are propylene glycol, polyethylene glycol, vegetable oils, such as olive oil and corn oil, gelatin, and injectable organic esters such as ethyl oleate.

The parenteral formulations described herein can also contain adjuvants such as preserving, wetting, emulsifying, and dispersing agents. The formulations are rendered sterile by incorporation of a sterilizing agent, filtration through a bacteria-retaining filter, irradiation, or heat.

The compounds of the invention can also be administered through the skin using conventional transdermal patch or other transdermal delivery system, wherein the conjugate is contained within a laminated structure that serves as a drug delivery device to be affixed to the skin. In such a structure, the compound is contained in a layer, or "reservoir," underlying an upper backing layer. The laminated structure can contain a single reservoir, or it can contain multiple reservoirs.

The compounds of the invention can also be formulated into a suppository for rectal administration. With respect to suppositories, the compound is mixed with a suppository base material which is (e.g., an excipient that remains solid at room temperature but softens, melts or dissolves at body temperature) such as coca butter (theobroma oil), polyethylene glycols, glycerinated gelatin, fatty acids, and combinations thereof. Suppositories can be prepared by, for example, performing the following steps (not necessarily in the order presented): melting the suppository base material to form a melt; incorporating the compound (either before or after melting of the suppository base material); pouring the melt into a mold; cooling the melt (e.g., placing the melt-containing mold in a room temperature environment) to thereby form suppositories; and removing the suppositories from the mold.

In some embodiments of the invention, the compositions comprising the compounds of the invention may further be incorporated into a suitable delivery vehicle. Such delivery vehicles may provide controlled and/or continuous release of the compounds and may also serve as a targeting moiety. Non-limiting examples of delivery vehicles include, adjuvants, synthetic adjuvants, microcapsules, microparticles, liposomes, and yeast cell wall particles. Yeast cells walls may be variously processed to selectively remove protein component, glucan, or mannan layers, and are referred to as whole glucan particles (WGP), yeast beta-glucan mannan particles (YGMP), yeast glucan particles (YGP), *Rhodotorula* yeast cell particles (YCP). Yeast cells such as *S. cerevisiae* and *Rhodotorula* species are preferred; however, any yeast cell may be used. These yeast cells exhibit different properties in terms of hydrodynamic volume and also differ in the target organ where they may release their contents. The methods of manufacture and characterization of these particles are described in U.S. Pat. Nos. 5,741,495, 4,810,646, 4,992,540, 5,028,703, 5,607,677, and U.S. Patent Application Publication Nos. 2005/0281781 and 2008/0044438.

The invention also provides a method for administering a compound of the invention as provided herein to a patient suffering from a condition that is responsive to treatment with the compound. The method comprises administering, generally orally, a therapeutically effective amount of the compound (preferably provided as part of a pharmaceutical preparation). Other modes of administration are also contemplated, such as pulmonary, nasal, buccal, rectal, sublingual, transdermal, and parenteral. As used herein, the term "parenteral" includes subcutaneous, intravenous, intra-arterial, intraperitoneal, intracardiac, intrathecal, and intramuscular injection, as well as infusion injections.

In instances where parenteral administration is utilized, it may be necessary to employ somewhat bigger oligomers than those described previously, with molecular weights ranging from about 500 to 30K Daltons (e.g., having molecular weights of about 500, 1000, 2000, 2500, 3000, 5000, 7500, 10000, 15000, 20000, 25000, 30000 or even more).

The method of administering may be used to treat any condition that can be remedied or prevented by administration of a particular compound of the invention. Those of ordinary skill in the art appreciate which conditions a specific compound can effectively treat. Exemplary conditions include conditions requiring anticonvulsant therapy and/or prophylaxis and pain. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 1000 mg, preferably in doses from 0.01 mg/day to 750 mg/day, and more preferably in doses from 0.10 mg/day to 500 mg/day.

The unit dosage of any given compound of the invention (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

All articles, books, patents, patent publications and other publications referenced herein are incorporated by reference in their entireties. In the event of an inconsistency between the teachings of this specification and the art incorporated by reference, the meaning of the teachings and definitions in this specification shall prevail (particularly with respect to terms used in the claims appended herein). For example, where the present application and a publication incorporated by reference defines the same term differently, the definition of the term shall be preserved within the teachings of the document from which the definition is located.

EXPERIMENTAL

It is to be understood that while the invention has been described in conjunction with certain preferred and specific embodiments, the foregoing description as well as the examples that follow are intended to illustrate and not limit the scope of the invention. Other aspects, advantages and modifications within the scope of the invention will be apparent to those skilled in the art to which the invention pertains.

All non-PEG chemical reagents referred to in the appended examples are commercially available unless otherwise indicated. The preparation of PEG-mers is described in, for example, U.S. Patent Application Publication No. 2005/0136031.

$^1$H NMR (nuclear magnetic resonance) data was generated by an NMR spectrometer.

Overview of Examples 1-5

Exemplary compounds of the invention (10µ, 18, 22, 23 and 24, where n is as defined in the specification, e.g., 2-11) can be prepared in accordance with the general approaches set forth in Examples 1-5.

Example 1

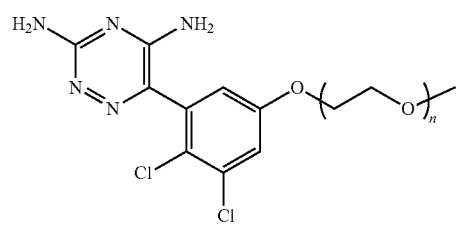

Example 2
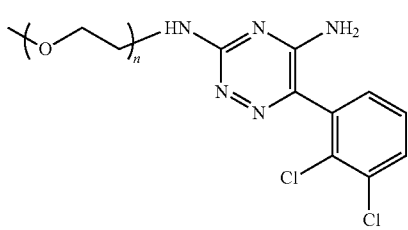
Examples 2 and 3
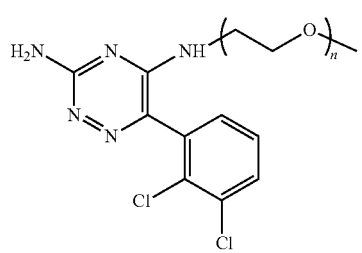
Example 4
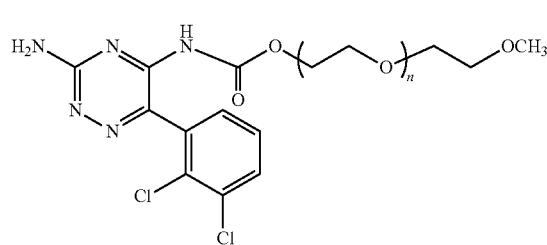
Example 5
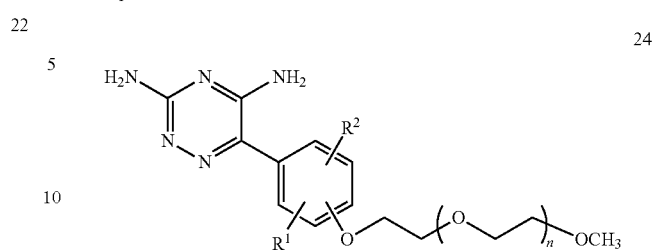
Example 1
Synthesis of mPEGn-O-Lamotrigine (Compound 10)
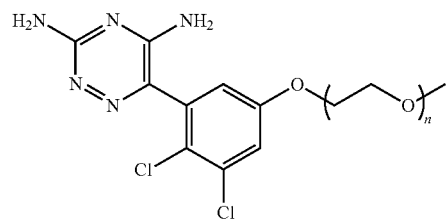
Schematically, an approach for preparing mPEGn-O-lamotrigine (Compound 10) is provided below.
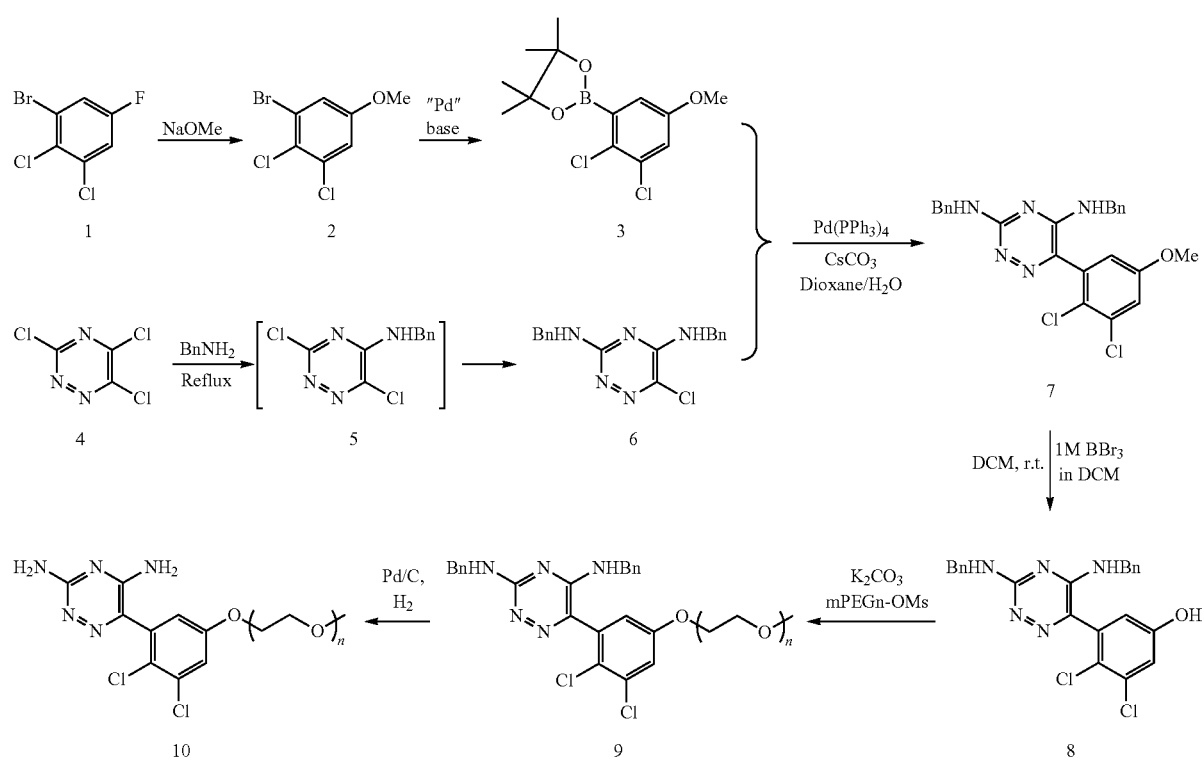

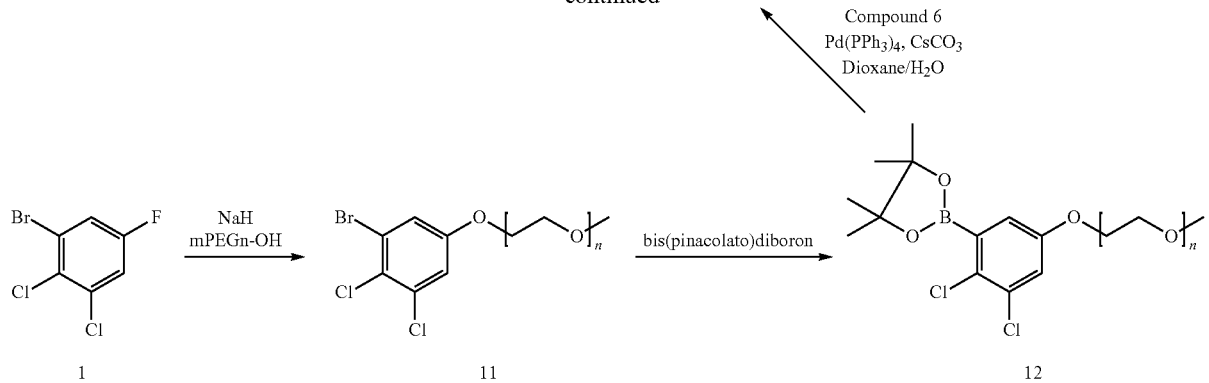

Descriptively, the approach can be carried out stepwise as follows.

Synthesis of 1-bromo-2.3-dichloro-5-methoxybenzene (Compound 2)

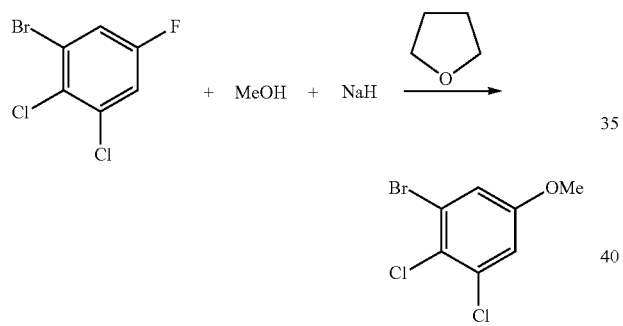

1-Bromo-2,3-dichloro-5-fluorobenzene (5.1453 g, 21.10 mmol) was dissolved in THF (25 mL) at room temperature and cooled to 0° C. Then, 5.1 g of sodium hydride (60%, 128 mmol) was added and 2.0 mL of methanol was added slowly. Additional THF (5 mL) was added. The mixture was stirred at room temperature for 10 minutes, then heated at 75° C. for four hours and cooled to room temperature. The mixture was poured into ice with some aq. sat. $NH_4Cl$ solution and extracted with EtOAc (3×100 mL). The organic solution was washed with brine, dried over $Na_2SO_4$, concentrated to dryness. The residue was purified with flash column chromatography on silica gel using hexane as solvent to afford the product (4.6727 g) as a white solid in 87% yield. $^1$H-NMR ($CDCl_3$): δ 7.109 (d, J=3.0 Hz, 1H), 6.988 (d, J=3.0 Hz, 1H), 3.786 (s, 3H). The product was also synthesized from 1-bromo-2,3-dichloro-5-fluorobenzene and sodium methoxide in THF. The final product was purified by recrystallization from hexane.

Synthesis of 2-(2,3-dichloro-5-methoxyphenyl)-4,4,5,5-tetramethyl-1,3-2-dioxaborolane (Compound 3)

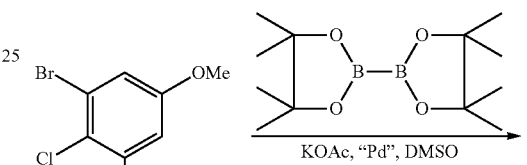

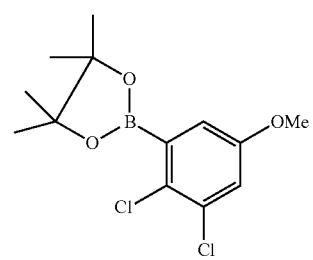

A mixture of 1-bromo-2,3-dichloro-5-methoxybenzene (9.3601 g, 36.6 mmol), bis(pinacolato)diboron (13.3339 g, 52.0 mmol), potassium acetate (10.7268 g, 109 mmol) and 1,1'-[bis(bisphenylphosphino)ferrocene]dichloropalladium (II) (1.32 g, 1.804 mmol) in anhydrous DMSO (100 mL) was stirred at 95° C. for 5.5 hours. The mixture was cooled to room temperature and poured into ice. The mixture was extracted with EtOAc (3×200 mL). The combined organic solution was washed with sat. NaCl solution (3×150 mL), dried over $Na_2SO_4$, and concentrated. The residue was purified with flash column chromatography on silica gel by using EtOAc/Hexane to afford 9.6970 g of product in 88% yield. $^1$H-NMR ($CDCl_3$): δ 7.092 (d, J=3.0 Hz, 1H), 7.050 (d, J=3.0 Hz, 1H), 3.794 (s, 3H), 1.368 (s, 9H).

Synthesis of 3,5-N,N-dibenzylamino-6-chloro-1,2,4-triazine (Compound 6)

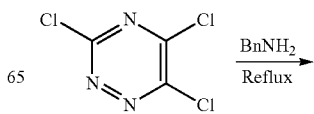

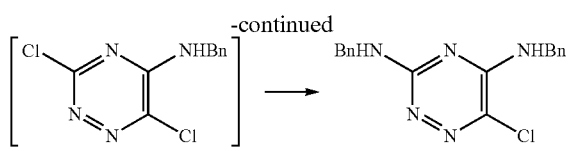

3,5,6-Trichloro-1,2,4-triazine (10.0967 g, 53.16 mmol) was dissolved in dioxane (250 mL) at room temperature to afford a yellow solution. Benzylamine (27 mL, 246 mmol) was added and a white suspension was observed. The resulting mixture was stirred at 115° C. for 5.5 hours. The mixture was cooled to room temperature and filtered to remove the white solid. The resulting white solid was washed with EtOAc. The solution was concentrated to afford 17.6979 g of crude product. The crude product was recrystallized with EtOAc to afford 16.3413 g of a slight yellow solid as the final produce in 94% yield. $^1$H-NMR (CDCl$_3$): δ 7.377-7.279 (m, 10H), 5.840 (s, 1H, NH), 5.620 (br, 1H, NH), 4.620 (d, J=5.5 Hz, 4H). $^{13}$C-NMR (DMSO): δ 151.01, 140.09, 138.56, 128.24, 128.11, 127.41, 127.16, 126.85, 126.52, 43.97, 43.04. LC-MS: 326.10 (MH$^+$/z).

Synthesis of N,N-dibenzyl-5-methoxy-lamotrigine (Compound 7)

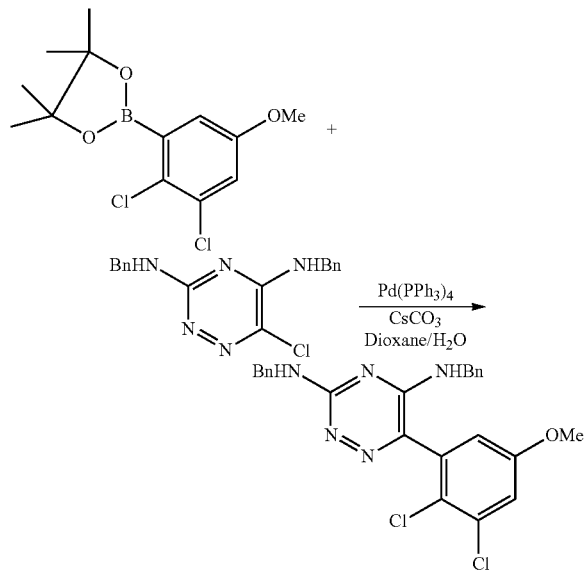

A mixture of the boronic ester (14.1461 g, 46.69 mmol), 3,5-dibenzylamino-6-chloro-1,2,4-triazine (13.3252 g, 40.90 mmol), cesium carbonate (20.3912 g, 62.0 mmol) and tetrakis(triphenylphosphine)palladium (2.6929 g, 2.33 mmol) in dioxane/water (180 mL/30 mL) was heated at 85° C. for 19 hours. The mixture was concentrated under reduced pressure to dryness. The residue was mixed with water and extracted with DCM (about 600 mL). At this point some precipitate remained in the mixture; therefore the mixture was filtered. The solid was washed with a small amount of acetone and ether. The solid was dried under high vacuum to afford the first crop of product (8.9986 g). The mother liquor was transferred into a separatory funnel. The organic solution was separated and washed with water, concentrated to remove 60% of DCM. Some precipitation was observed. The mixture was warmed using a heat gun and then cooled. The solid was collected to afford second crop of product (5.185 g). $^1$H-NMR (CDCl$_3$): δ 7.368-7.229 (m, 10H), 7.102 (d, J=3.0 Hz, 1H), 6.912 (d, J=3.0 Hz, 1H), 5.500 (br, 1H, NH), 4.959 (br, 1H, NH), 4.660-4.548 (m, 4H), 3.795 (s, 3H, OMe). LC-MS: 466.1 (MH$^+$/z).

Synthesis of N,N-dibenzyl-5-hydroxy-lamotrigine (Compound 8)

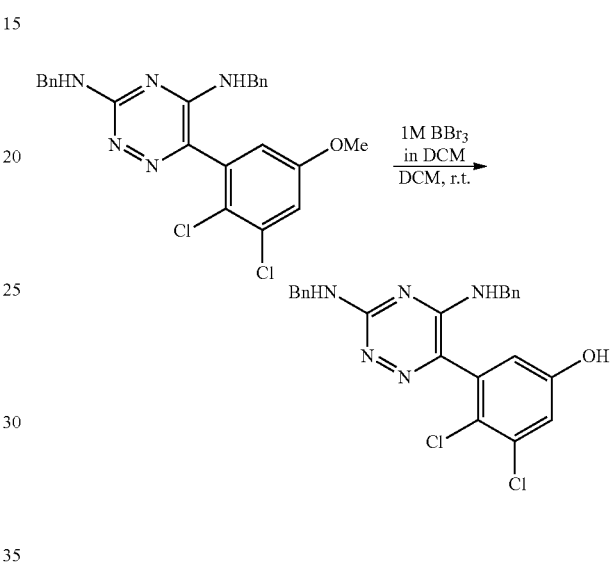

N,N-Dibenzyl-5-methoxy lamotrigine (0.5479 g, 1.175 mmol) was mixed with DCM (40 mL) to afford a white suspension. The mixture was cooled to 0° C., and then boron tribromide in DCM (1.0 M solution) (1.75 mL, 1.75 mmol) was added to afford a clear slightly yellow solution. The resulting solution was stirred at room temperature for 4.5 hours. An additional amount of BBr$_3$ in DCM solution (2.0 mL, 2.0 mmol) was added. The mixture was stirred at room temperature for another two hours. Methanol was added to quench the reaction and the reaction was concentrated. The resulting residue was dissolved in DCM and 5% aq. NaHCO$_3$ was added. A white suspension was obtained. The bottom layer containing the white suspension was separated and the upper layer was extracted with DCM (2×15 mL). The combined organic solution was washed with sat. NH$_4$Cl, concentrated and the white residue was dried under high vacuum overnight. The residue appeared to contain some inorganic salt and was subsequently dissolved in EtOAC and washed with water. The separation of layers was very difficult at which point aq. NaHCO$_3$ solution was added. The organic layer was separated and dried over Na$_2$SO$_4$, concentrated to afford 0.5322 g of crude product. Based on TLC, the product still contained impurities but the material can be carried forward without further purification to the next step. $^1$H-NMR (CDCl$_3$): δ 7.309-7.234 (m, 10H), 7.096 (d, J=1.5 Hz, 1H), 6.987 (s, 1H), 5.767 (br, 1H, NH), 5.294 (s, 1H, NH), 4.700-4.505 (m, 4H). LC-MS: 450.1 (MH$^+$/z).

Synthesis of N,N'-dibenzyl-mPEGn-O-lamotrigine (Compound 9)

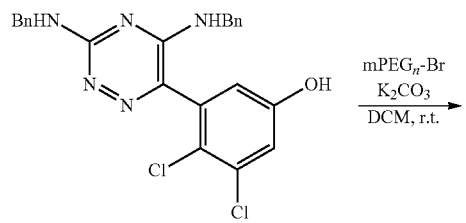

A mixture of N,N-dibenzyl-5-hydroxy-lamotrigine 8 (3.05 mmol) and mPEG$_n$-Br (3.65 mmol, 1.2 eq) in the presence of potassium carbonate (16.83 mmol) in dichloromethane is allowed to stir at room temperature for 17 hours. The mixture is cooled to room temperature and then is filtered and washed with acetone and DCM. The solution is concentrated. The residue is purified by column chromatography on silica gel to afford pure product (Compound 9).

Synthesis of mPEGn-O-Lamotrigine (Compound 10)

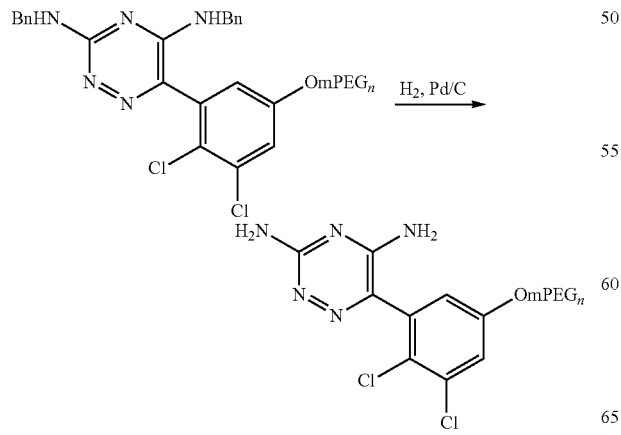

To a solution of N,N'-dibenzyl-mPEGn-O-lamotrigine (0.74 mmol) in EtOAc (10 mL) is added Pd/C (10%). The mixture is stirred at room temperature under an H$_2$ atmosphere (30 psi) for 4.0 hours. The reaction mixture is filtered over Celite, and the filter cake is washed with EtOAc. Removal of solvent under reduced pressure affords the corresponding aromatic amine (Compound 10).

Example 2

Synthesis of mPEGn-N-Lamotrigine (Compound 22) and mPEGn-N-Lamotrigine (Compound 18)

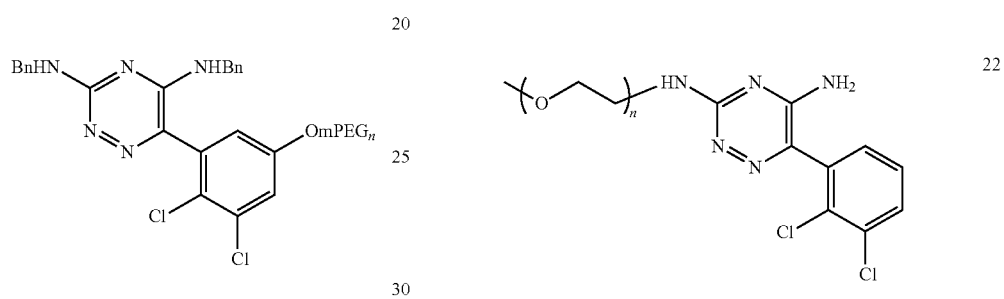

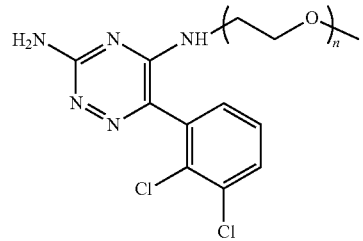

Schematically, an approach for preparing each of mPEGn-N-Lamotrigine (Compound 22) and mPEGn-N-Lamotrigine (Compound 18) is provided below.

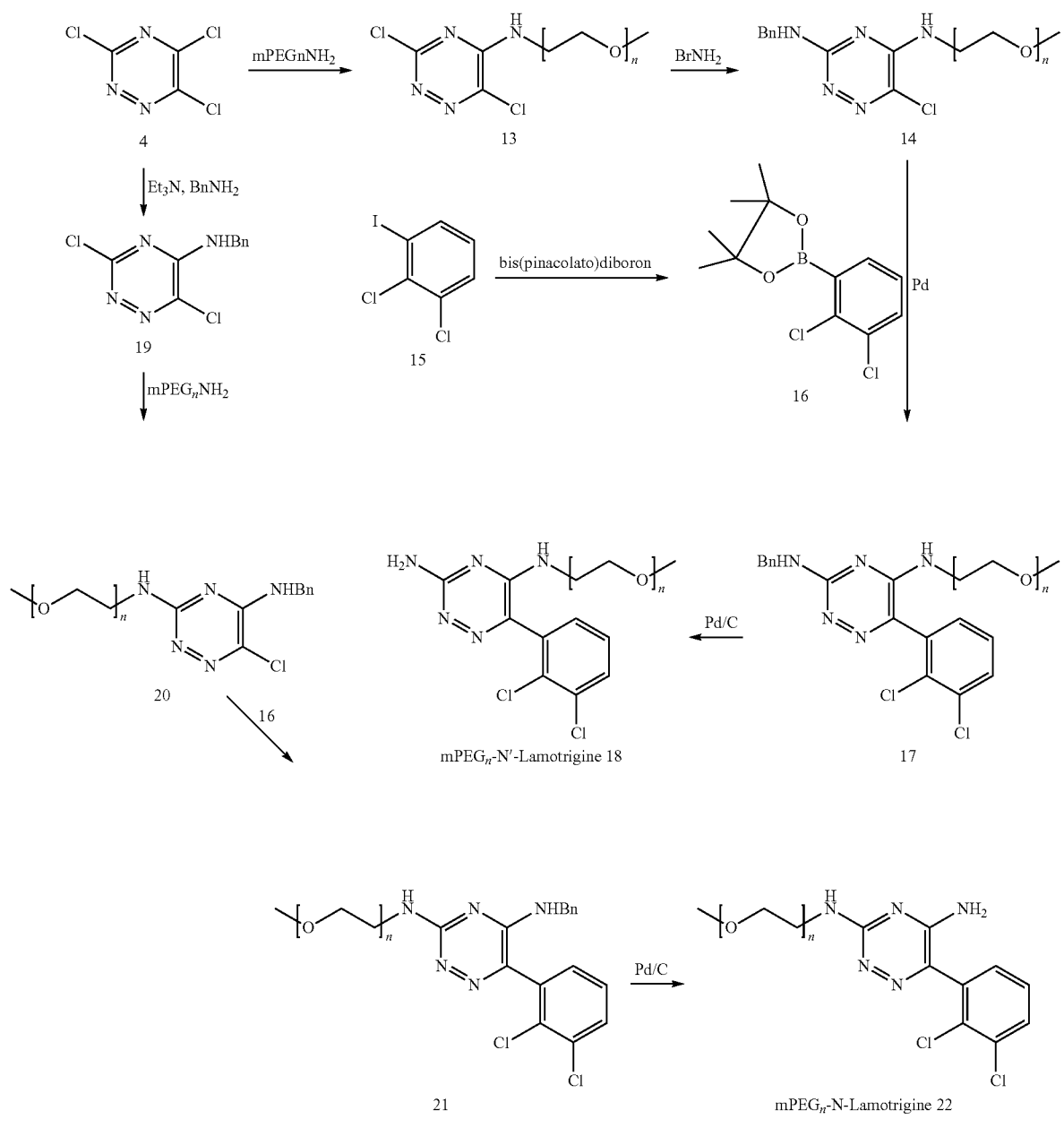

Descriptively, an approach for preparing mPEGn-N-Lamotrigine (Compound 22) can be carried out stepwise as follows.

Synthesis of 2-(2,3-dichlorophenyl)-4,4,5,5-tetramethyl-1,3-2-dioxaborolane (Compound 16)

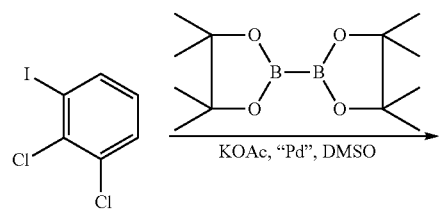

-continued

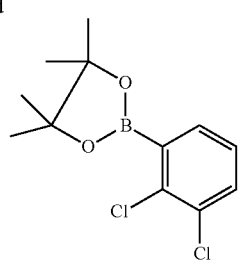

A mixture of 1,2-dichloro-3-iodobenzene (7.9229 g, 28.50 mmol), bis(pinacolato)diboron (12.8674 g, 50.20 mmol), potassium acetate (8.0214 g, 82 mmol) and 1,1'-[bis(bisphenyl phosphino)ferrocene]dichloropalladium (II) (1.010 g, 1.38 mmol) in anhydrous DMSO (88 mL) was stirred at room temperature for ten minutes at 85° C. (oil bath temperature) for 4.5 hours. The mixture was cooled to room temperature and poured into ice. The mixture was extracted with EtOAc (3×150 mL). The combined organic solution was washed with sat. NaCl (3×100 mL), dried over $Na_2SO_4$, and concentrated. The resulting residue was purified with flash column chromatography on silica gel to afford 5.7869 g of the desired product as white solid in 74.5% yield. $^1$H-NMR ($CDCl_3$): δ 7.557 (dd, J=7.0-8.0 Hz and 1.5 Hz, 1H), 7.050 (dd, J=7.5-8.0 Hz and 1.5 Hz, 1H), 7.172 (d, J=7.5-8.0 Hz, 1H), 1.368 (s, 9H).

Synthesis of 5-N-benzylamino-3,6-dichloro-1,2,4-triazine (Compound 19)

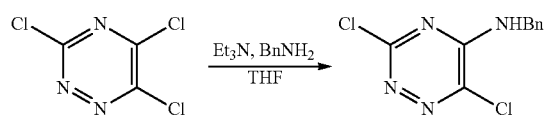

3,5,6-Trichloro-1,2,4-triazine (11.6191 g, 61.2 mmol) was dissolved in THF (150 mL) at room temperature to afford a yellow solution. Triethylamine (13.0 mL, 93 mmol) was added. The solution was cooled to about −10° C. (ice/NaCl) and benzylamine (6.6166 g, 61.4 mmol) was added. The reaction mixture was stirred for 30 minutes at this temperature, and then for 30 minutes at 0° C. The mixture was filtered to remove the solid which was washed with EtOAc. The combined solution was concentrated to dryness. The resulting brown solid was dried under vacuum. The crude product (17.2841 g) was recrystallized from EtOH to afford 13.8653 g of a pink needle solid as product. The yield was 89%. $^1$H-NMR ($CDCl_3$): δ 7.416-7.351 (m, 5H), 6.151 (s, 1H, NH), 4.724 (d, J=5.5 Hz, 2H). $^{13}$C-NMR ($CDCl_3$), 161.79, 152.38, 142.83, 135.79, 129.06, 128.41, 128.32, 45.37. LC-MS: 255.1 ($MH^+$/z). Reference: Nyffenegger, C.; Fournet, G.; Joseph, B. *Tetrahedron Letters*, 48, 5069-5072, 2007.

Synthesis of 5-N-benzylamino-3-N-mPEG$_3$-6-chloro-1,2,4-triazine (Compound 20)

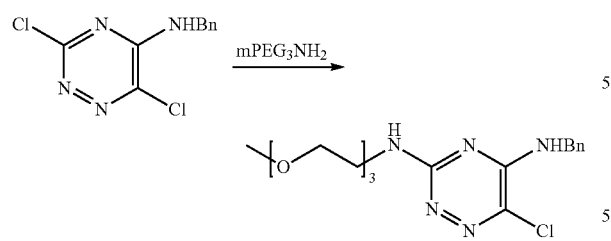

5-Benzylamino-3,5-dichloro-1,2,4-triazine (641 mg, 2.51 mmol) was dissolved in dioxane (15 mL) at room temperature. Triethylamine (0.7 mL, 5.02 mmol) was added, followed by addition of mPEG$_3$-NH$_2$ (581.7 mg, 3.56 mmol). The resulting mixture was stirred at 85° C. for 23 hours. The mixture was cooled to room temperature, filtered to remove the white solid and the solid was washed with EtOAc. The combined organic solution was concentrated and purified with flash column chromatography on silica gel to afford product (0.960 g). $^1$H-NMR ($CDCl_3$): δ 7.395-7.317 (m, 5H), 5.765 (s, 1H, NH), 5.550 (br, 1H), 3.668-3.555 (m, 12H), 3.383 (s, 3H, OMe). LC-MS: 382.2 ($MH^+$/z).

Synthesis of 5-N-benzylamino-3-mPEG$_n$-N-Lamotrigine (Compound 21)

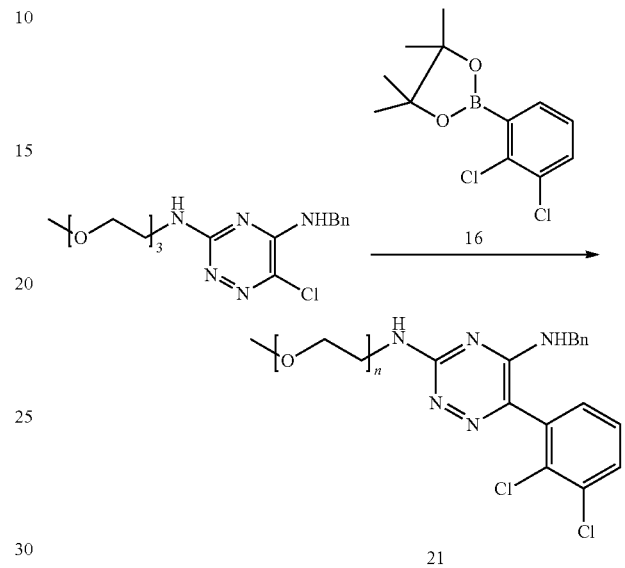

A mixture of the boronic ester (46.69 mmol), 5-N-benzylamino-3-N-mPEG$_n$-6-chloro-1,2,4-triazine (40.90 mmol), cesium carbonate (62.0 mmol) and tetrakis(triphenylphosphine)palladium (2.33 mmol) in dioxane/water (180 mL/30 mL) is heated at 85° C. for 19 hours. The mixture is concentrated under reduced pressure to dryness. The residue is mixed with water and is extracted with DCM (about 600 mL). At this point some precipitate may remain in the mixture; therefore the mixture can be filtered. The solid is washed with a small amount of acetone and ether. The solid is then dried under high vacuum to afford the first crop of product. The mother liquor is transferred into a separatory funnel. The organic solution is separated and is washed with water, and is concentrated to remove 60% of DCM. Some precipitation may be observed. The mixture can be warmed using a heat gun and then cooled. The solid is collected to afford a second crop of product.

Synthesis of mPEG$_n$-N-Lamotrigine (Compound 22)

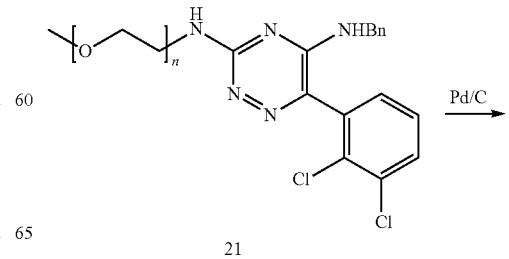

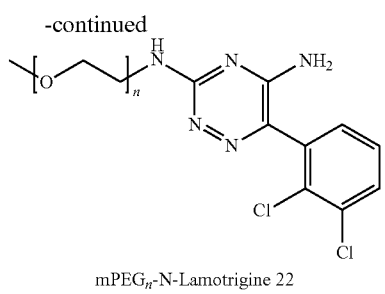

mPEG$_n$-N-Lamotrigine 22

To a solution of compound 21 (0.74 mmol) in EtOAc (10 mL) is added Pd/C (10%). The mixture is stirred at room temperature under an H$_2$ atmosphere (30 psi) for 4.0 hours. The reaction mixture is filtered over Celite, and the filter cake is washed with EtOAc. Removal of solvent under reduced pressure affords the corresponding aromatic amine (Compound 22).

Example 3

A General Procedure for the Synthesis of mPEG$_n$-N-Lamotrigine (Compound 18)

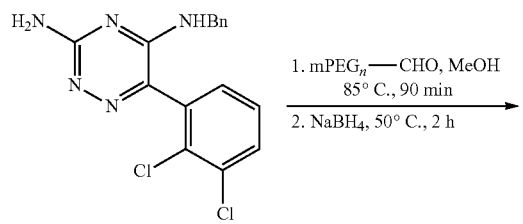

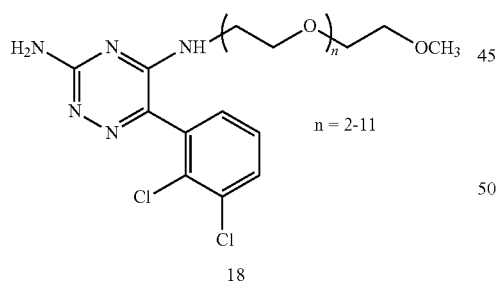

18

A solution of Lamotrigine (98 mg, 0.20 mmol) (with the —NH$_2$ group at 3-position of the triazine ring protected), and mPEG$_n$-CHO (n=3, 5 or 7) (0.30 mmol) in CH$_3$OH (10 mL) is stirred at 85° C. under azeotropic conditions for 90 min. (4.0 ml of CH$_3$OH is removed). After this period, the reaction mixture is cooled to room temperature and sodium borohydride (20 eq.) is added in portions. The mixture is stirred at 50° C. for 2 h, and then the reaction is quenched with sodium bicarbonate. 150 ml of DCM is added. The solution is washed with H$_2$O (3×150 ml). The organic phase is dried over sodium sulfate and is then concentrated under reduced pressure. The residue is purified by column chromatography over silica gel.

Example 4

A General Procedure for the Synthesis of mPEG$_n$-OCN-Lamotrigine (Compound 23)

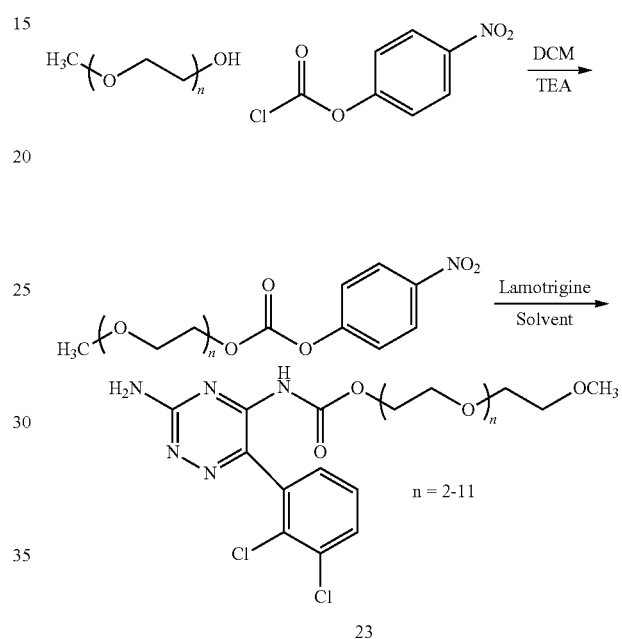

mPEG$_n$-OH Carbonate Activation:

In a 50-mL flask, mPEG, —OH (~2 mmol) is dissolved in freshly distilled DCM (3 mL). 4-Nitrophenylchloroformate is added and after a homogeneous solution is obtained, TEA (1.5 eq) is added. The reaction is kept at ambient temperature in a water bath the reaction is monitored by analytical HPLC until complete. The reaction is quenched with ammonium chloride and extracted with DCM (20 mL×3). The combined organic layers are dried over Na$_2$SO$_4$, filtered, and concentrated under reduced pressure to give a product mixture. The residue is used in the following reaction after drying under high vacuum for 30 min without further purification.

mPEG$_n$-OCN-Lamotrigine:

The above carbonate precursor is suspended in acetonitrile (8 mL) and water (8 mL). Lamotrigine (1 eq) (with the —NH$_2$ group at 3-position of the triazine ring protected), and Na$_2$CO$_3$ (2 eq) are added and the reaction is kept at ambient temperature overnight. Upon completion, the reaction is quenched with ammonium chloride (50 mL) and the basic solution is neutralized to pH=6-7 using 10% of HOAc. The resulting solution is then extracted with DCM (20 mL×3) and the combined organic layers are dried over Na$_2$SO$_4$, filtered, and concentrated under reduced pressure. The residue is purified using Biotage flash chromatography.

Example 5

A General Procedure for the Synthesis of mPEG$_n$-O-Lamotrigine (Compound 24)

R$^1$ and R$^2$ are independently Cl, Br, I, C$_{1-4}$ alkyl, or —OMe

What is claimed is:

1. A compound encompassed by the following formula:

or a pharmaceutically acceptable salt thereof, wherein:
R$^1$ is selected from the group consisting of Cl, Br, I, C$_{1-4}$ alkyl and OMe;
R$^2$ is selected from the group consisting of Cl, Br, I, C$_{1-4}$ alkyl and OMe; and
n is an integer selected from the group consisting of 2, 3, 4, 5, 6, 7, 8, 9, 10 and 11.

2. The compound of claim 1, wherein: R$^1$ is selected from the group consisting of Cl, Br, I, and C$_{1-4}$ alkyl; and R$^2$ is selected from the group consisting of Cl, Br, I, and C$_{1-4}$ alkyl.

3. The compound of claim 1, wherein: R$^1$ is selected from the group consisting of Cl, Br and I; and R$^2$ is selected from the group consisting of Cl, Br and I.

4. The compound of claim 1, wherein R$^1$ is Cl and R$^2$ is Cl.

5. The compound of claim 4, wherein n is selected from the group consisting of 2, 3, 4, 5 and 6.

6. The compound of claim 5, wherein n is 2.

7. The compound of claim 5, wherein n is 3.

8. The compound of claim 5, wherein n is 4.

9. The compound of claim 5, wherein n is 5.

10. The compound of claim 1, wherein n is selected from the group consisting of 2, 3, 4, 5 and 6.

11. The compound of claim 1, wherein n is 2.

12. The compound of claim 1, wherein n is 3.

13. The compound of claim 1, wherein n is 4.

14. The compound of claim 1, wherein n is 5.

\* \* \* \* \*